US008435492B2

(12) United States Patent
Hunter et al.

(10) Patent No.: US 8,435,492 B2
(45) Date of Patent: May 7, 2013

(54) PROSTHETIC GROUPS ATTACHED TO STANNYL POLYMER IN THE SYNTHESIS OF RADIOPHARMACEUTICALS

(75) Inventors: Duncan Hunter, London (CA); M. Karen J. Gagnon, Moose Jaw (CA)

(73) Assignee: University of Western Ontario, London, Ontario (CA)

( * ) Notice: Subject to any disclaimer, the term of this patent is extended or adjusted under 35 U.S.C. 154(b) by 895 days.

(21) Appl. No.: 10/555,248

(22) PCT Filed: Apr. 30, 2004

(86) PCT No.: PCT/IB2004/001834
§ 371 (c)(1),
(2), (4) Date: Dec. 20, 2006

(87) PCT Pub. No.: WO2004/098650
PCT Pub. Date: Nov. 18, 2004

(65) Prior Publication Data
US 2007/0155976 A1 Jul. 5, 2007

Related U.S. Application Data

(60) Provisional application No. 60/467,752, filed on May 2, 2003.

(51) Int. Cl.
*A61K 51/00* (2006.01)
(52) U.S. Cl.
USPC ........................................................ 424/1.85
(58) Field of Classification Search .................. None
See application file for complete search history.

(56) References Cited

U.S. PATENT DOCUMENTS

| 4,631,211 A | 12/1986 | Houghten et al. |
| 5,143,854 A | 9/1992 | Pirrung et al. |
| 5,288,514 A | 2/1994 | Ellman et al. |
| 5,359,115 A | 10/1994 | Campbell et al. |

(Continued)

FOREIGN PATENT DOCUMENTS

| EP | 0989120 B1 | 1/2003 |
| WO | WO 91/07087 | 5/1991 |

(Continued)

OTHER PUBLICATIONS

Jerry March, "Advanced Organic Chemistry," 1992, pp. 352-357.*

(Continued)

*Primary Examiner* — Brian Gulledge
(74) *Attorney, Agent, or Firm* — John M. Garvey; Pei Wu; K&L Gates LLP

(57) ABSTRACT

The present invention relates to compositions and methods for preparing radiopharmaceutical compounds in high chemical-purity and isotopic-purity. The present invention provides polymer-bound precursors to radiopharmaceutical compounds that can be converted to radiopharmaceutical compounds in one step. In a preferred embodiment, a radiopharmaceutical precursor is bound to a polymeric support via a prosthetic group comprising an alkenyl-tin bond. The radiopharmaceutical precursor is converted to a radiopharmaceutical compound in one step involving cleavage of the alkenyl-tin bond and incorporation of a radioisotope to form the radiopharmaceutical compound. Importantly, the polymeric support containing the toxic tin by-product can be easily removed from the radiopharmaceutical compound by filtration. The present invention can be used to install a large number of different radioisotopes. In a preferred embodiment, the radioisotope is [211]At, $^{123}$I or [131]I.

46 Claims, 15 Drawing Sheets

U.S. PATENT DOCUMENTS

| | | | |
|---|---|---|---|
| 5,362,899 | A | 11/1994 | Campbell et al. |
| 5,440,016 | A | 8/1995 | Blondelle et al. |
| 5,480,971 | A | 1/1996 | Houghten et al. |
| 5,565,185 | A | 10/1996 | Hunter et al. |
| 5,840,859 | A * | 11/1998 | Lambert et al. ............. 534/10 |
| 6,365,125 | B1 | 4/2002 | Hiltunen et al. |

FOREIGN PATENT DOCUMENTS

| | | |
|---|---|---|
| WO | WO 92/10092 | 6/1992 |
| WO | WO 93/09668 | 5/1993 |
| WO | WO 93/20242 | 10/1993 |
| WO | WO 94/08051 | 4/1994 |
| WO | WO98/18499 | 5/1998 |
| WO | 98/56763 A1 | 12/1998 |
| WO | WO99/18053 | 4/1999 |
| WO | WO 99/18053 * | 4/1999 |
| WO | WO02/070020 | 9/2002 |
| WO | WO03/002489 | 1/2003 |
| WO | WO2004/056399 | 7/2004 |

OTHER PUBLICATIONS

Geysen HM, et al., "Use of peptide synthesis to probe viral antigens for epitopes to a resolution of a single amino acid", Proc Natl Acad Sci U.S.A, vol. 81, 1984, pp. 3998-4002.

Houghten RA., "General method for the rapid solid-phase synthesis of large numbers of peptides: specificity of antigen-antibody interaction at the level of individual amino acids", Proc Natl Acad Sci U.S.A., vol. 82, 1985, pp. 5131-5135.

Needels MC, et al., "Generation and screening of an oligonucleotide-encoded synthetic peptide library", Proc Natl Acad Sci U S A, vol. 90, 1993, pp. 10700-10704.

Burbaum JJ, et al., "A paradigm for drug discovery employing encoded combinatorial libraries", Proc Natl Acad Sci U.S.A., 1995, vol. 92, pp. 6027-6031.

Ohlmeyer MH, et.al., "Complex synthetic chemical libraries indexed with molecular tags", Proc Natl Acad Sci U S A., 1993, vol. 90, pp. 10922-10926.

International Search Report, PCT/IB2004/001834, mailed Oct. 12, 2004.

Brenner S, et al., "Encoded combinatorial chemistry", Proc. Natl. Acad. Sci., USA, 1992, vol. 89, pp. 5381-5383.

Hunter DH, et al., "Polymer supported radiopharmaceuticals: 131I MIBG and 123I MIBG", Journal of Labelled Compounds and Radiopharmaceuticals, vol. 42, 1999, pp. 653-661.

Whitfield DM, et al., "Polymer supported tin carbohydrate chemistry", Glyconcojugate Journal, vol. 15, 1998, pp. 75-78.

Culbert PA, et al., "Polymer-supported radiopharmaceuticals: 123-I- and 131-I-labeled N-isopropyl-4-iodoamphetamine", Reactive Polymers, Elsevier Science Publishers, Amsterdam, NL, vol. 19, 1993, pp. 247-253, Abstract.

Gagnon, et al., "Development of a Polymer-Supported Prosthetic Group En Route to Rapid Radiopharmaceutical Production", Journal of Nuclear Medicine, vol. 44, No. 5, Suppl., 2003, p. 315P, Abstract No. 1128.

Examination Report—EP 04730617 dated Sep. 3, 2010.

Notice of Reasons for Rejection and claims (translated) cited in corresponding JP case, JP Application No. 2010-149018, issued by Japan Patent Office dated Oct. 25, 2012 (6 pages).

* cited by examiner insoluble polymeric precursor     soluble radioiodinated propenyl product     insoluble polymeric sideproduct

PROSTHETIC GROUPS ATTACHED TO STANNYL POLYMER IN THE SYNTHESIS OF RADIOPHARMACEUTICALS

RELATED APPLICATION

This application claims the benefit of priority to U.S. Provisional Patent Application Ser. No. 60/467,752, filed May 2, 2003.

BACKGROUND OF THE INVENTION

Molecules labeled with radioactive isotopes have been used as both imaging agents in medical diagnosis as well as therapeutic agents in the treatment of cancer. Both radiolabeled small molecules and radiolabeled peptides and nucleosides have been used to diagnose tumors. In addition to their use as diagnostic tools, radiolabeled nucleotides have been used to treat tumors in mammals by injecting or infusing radiolabeled nucleosides directly to the affected site.

One practical issue associated with the use of radioisotopes is the means by which the radioactive isotope is bound to the delivery molecule. This is important because it is often the case that a molecule with special binding properties will be used to deliver a radioactive isotope to a specific location ill an organism. Hence, it is critical that the functional groups used to bind the radioisotope do not alter the binding specificity of the delivery molecule. Furthermore, the radioisotope should be strongly bound to the delivery molecule because inadvertent release of the radioisotope would unnecessarily subject healthy tissue to radiation.

One common method of labeling molecules with radioactive isotopes for medical use is a stannylation process. See U.S. Pat. No. 5,565,185. Although this process yields isotopically pure products, toxic tin by-products often remain and must be separated before the radiolabeled molecules can be used. In addition, the unstable nature of radiolabeled molecules and their precursors lead to a short shelf-life. Hence, a method for attaching the radioisotope to a wide variety of molecules that avoids toxic side products would be highly desirable.

Radiolabeling of biosequences may also be achieved with activated esters. This method presents a similar problem of chemical purity and isotopic purity. While it is possible to attach a radioactive agent, for example, a benzamide, to a protein or peptide, only a small fraction of the resulting proteins or peptides actually bear the radioactive tag. Separation of the radiolabeled material from non-radiolabeled material is particularly difficult since the protein or peptide is very large and the tag represents only a minor structural modification.

One technique used to simplify the purification of compounds is to attach the desired molecule to a solid support. This approach allows one to simply wash away unwanted contaminants leaving the essentially pure compound attached to the solid support. This technique can be advantageous when the desired product and the contaminants are difficult to separate using standard separation procedures such as extraction or chromatography. See WO 02/070020 and WO 99/18053 for additional discussion of the advantages relating to solid-phase synthesis.

In addition, organic synthesis on insoluble supports is a rapidly developing methodology which offers several advantages compared to traditional synthesis in solution. In recent years many new synthetic methods for solid-phase synthesis have been developed, and this technique is becoming a valuable alternative to traditional synthesis. Solid-phase synthesis is particularly useful when large numbers of different compounds in small quantities are needed for screening assays. Combinatorial chemistry and the production of compound libraries are usually based on solid-phase synthesis.

Therefore, the need exists for a procedure to prepare radiolabeled molecules and biosequences in high chemical purity and isotopic purity. Furthermore, there is a need for precursors to radiolabeled molecules that have a long shelf-life. The present invention fulfills the above-mentioned needs and has other related advantages.

SUMMARY OF THE INVENTION

The invention relates generally to a method of using prosthetic groups to prepare radiopharmaceutical compounds. One aspect of the present invention relates to a polymer-bound alkenylstannane that contains an amino functional group. In certain preferred embodiments, the amino functional group is a piperidine ring. In another preferred embodiment, the polymer-bound alkenylstannane contains a leaving group that can be displaced by a nucleophile. This allows for functionalization of a nucleophilic compound by a prosthetic group that can then be converted to a radiopharmaceutical compound by cleavage of the alkenyl-stannane bond. Another aspect of the present invention relates to a method for preparing a polymer-bound prosthetic group comprising attaching an alkene to the surface of a polymer by an alkene-tin bond. The leaving group of the prosthetic group is subsequently unmasked. In a preferred embodiment, the leaving group is a mesylate. Another aspect of the present invention relates to a method of preparing a radiopharmaceutical compound from a functionalized prosthetic group comprising the step of mixing a radioisotope, oxidant, and functionalized prosthetic group. In preferred embodiments, the radioisotope is $^{211}$At, $^{123}$I, or $^{131}$I, and the oxidant is chloramine-T in ethanol/water.

DETAILED DESCRIPTION OF THE INVENTION

Overview of a Preferred Embodiment

Figure 1:
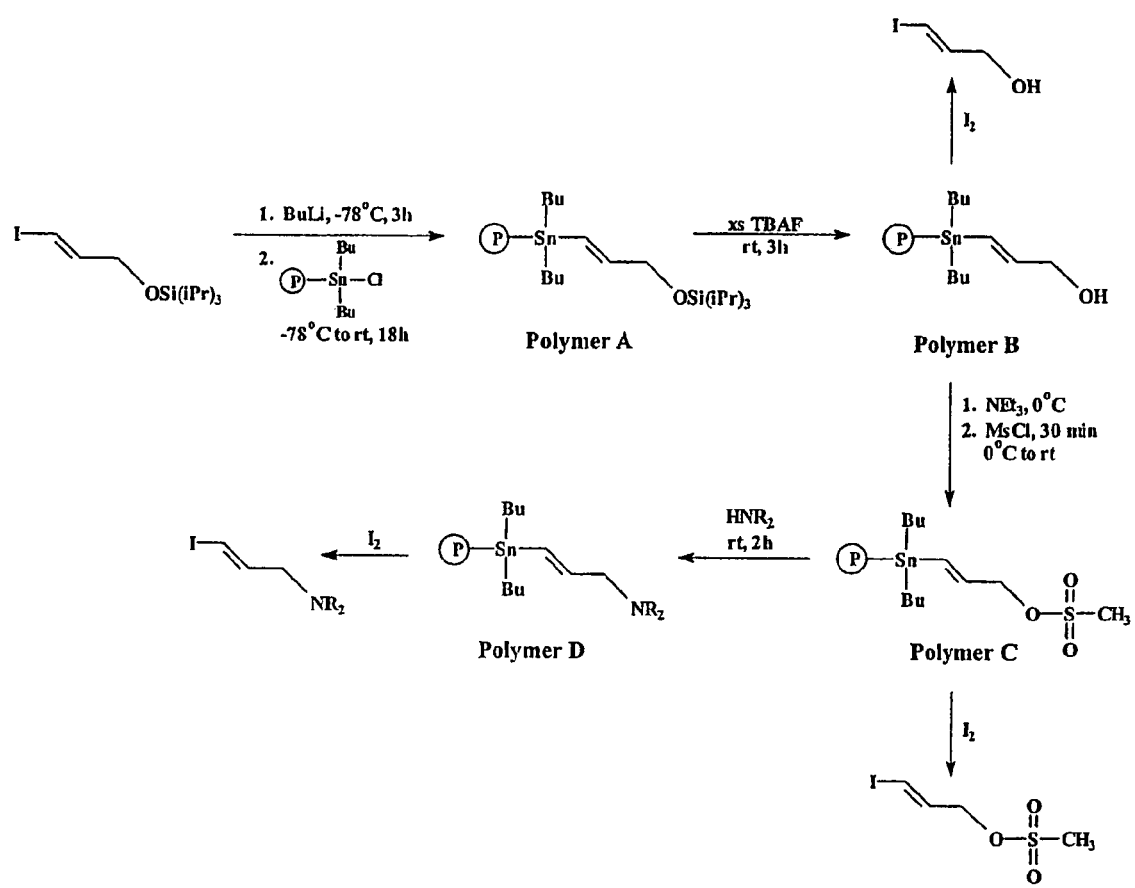
FIG. 1 depicts a route for the synthesis of a polymer-bound propenyl amine.
Figure 2:
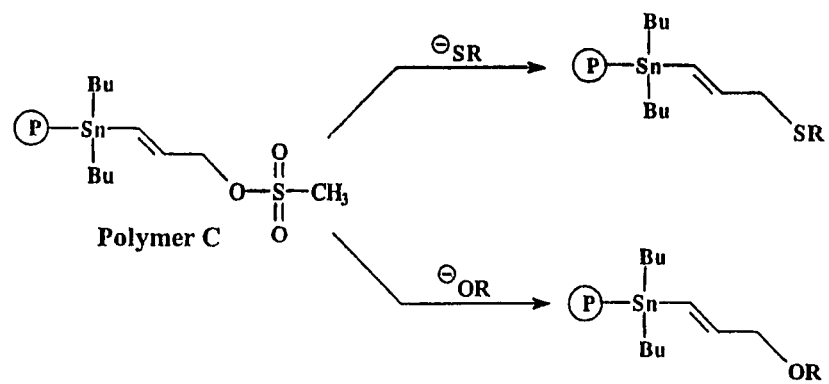
FIG. 2 depicts a route for the synthesis of a polymer-bound propenyl thioether and ether.
Figure 3:
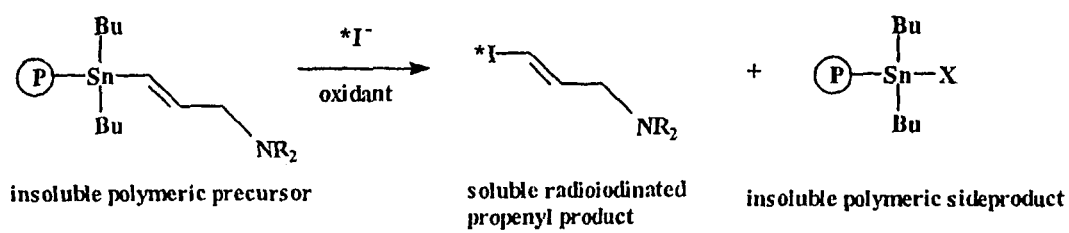
FIG. 3 depicts a route for the synthesis of a radiopharmaceutical compound.
Figure 4:
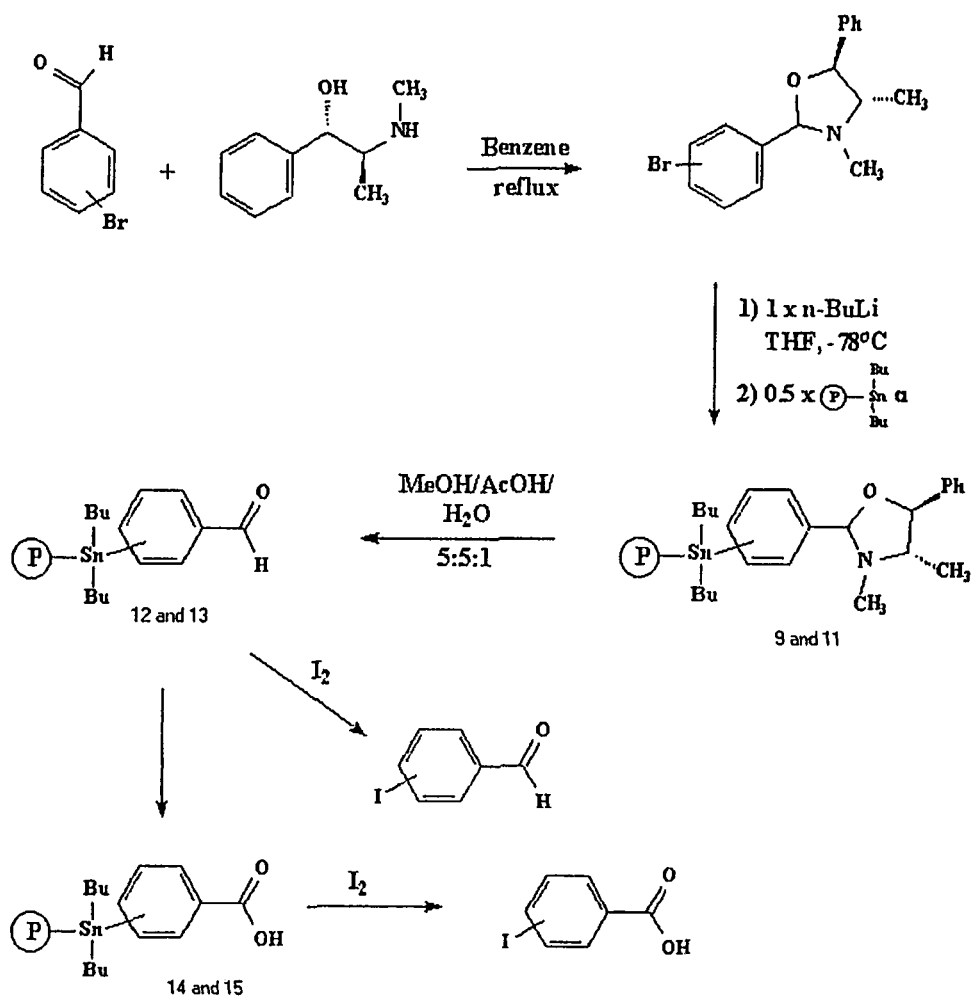
FIG. 4 depicts a route for the synthesis of polymer-bound arylstannanes.
Figure 5:
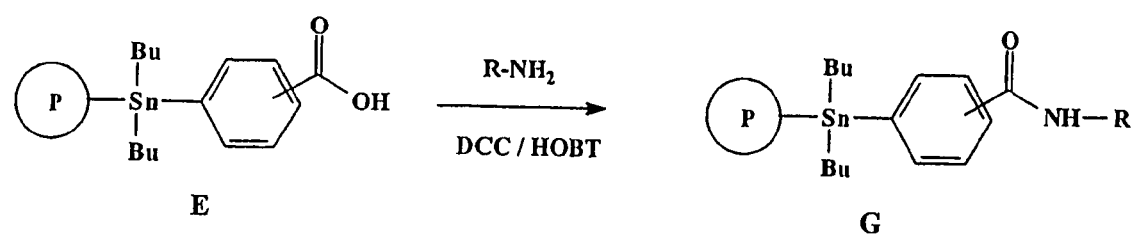
FIG. 5 depicts a route for the synthesis of polymer-bound arylstannanes. Note: DCC refers to dicyclohexylcarbodiimide. HOBT refers to hydroxybenzotriazide.
Figure 6:
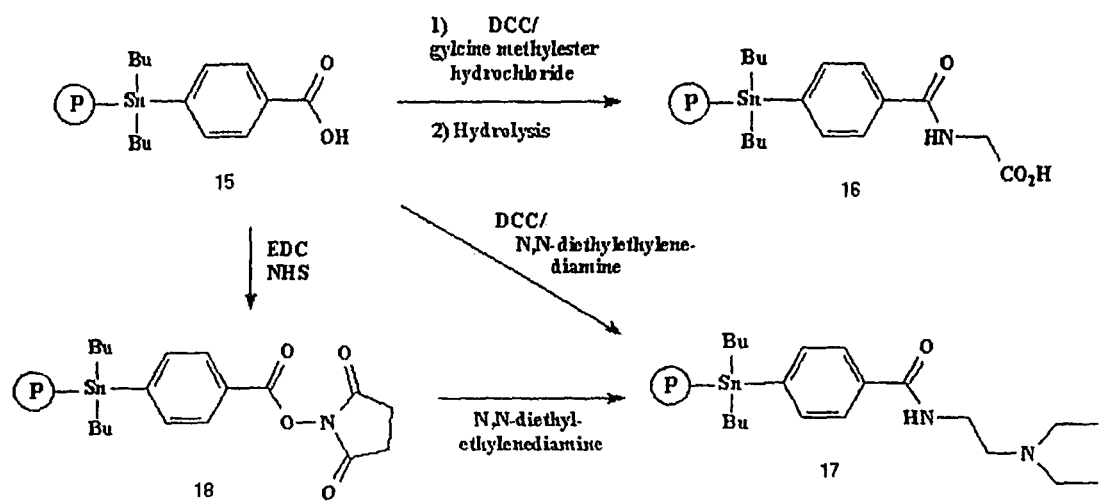
FIG. 6 depicts a route for the synthesis of polymer-bound arylstannanes.
Figure 7:
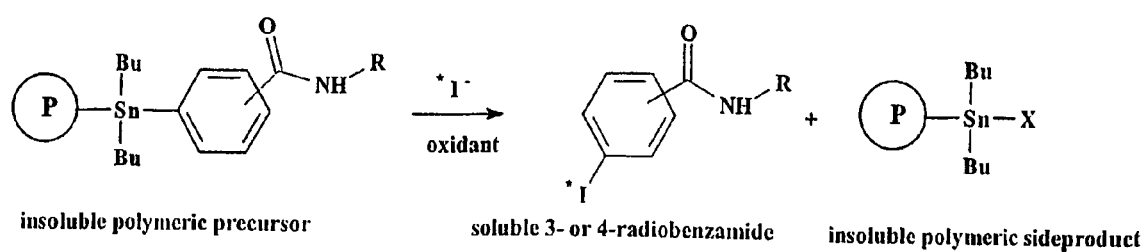
FIG. 7 depicts a route for the synthesis of an aromatic radiopharmaceutical compound.
Figure 8:
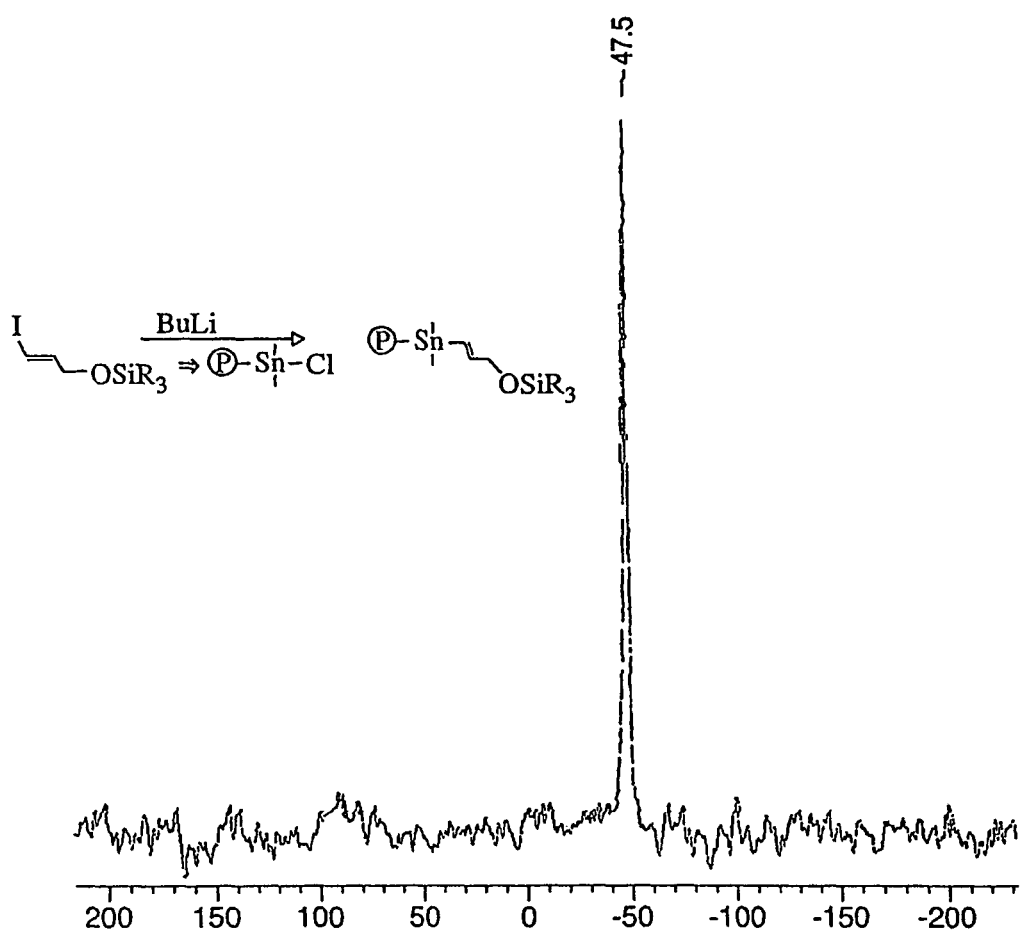
FIG. 8 depicts a $^{119}$Sn NMR spectrum of a polymer-bound propenylstannane.
Figure 9:
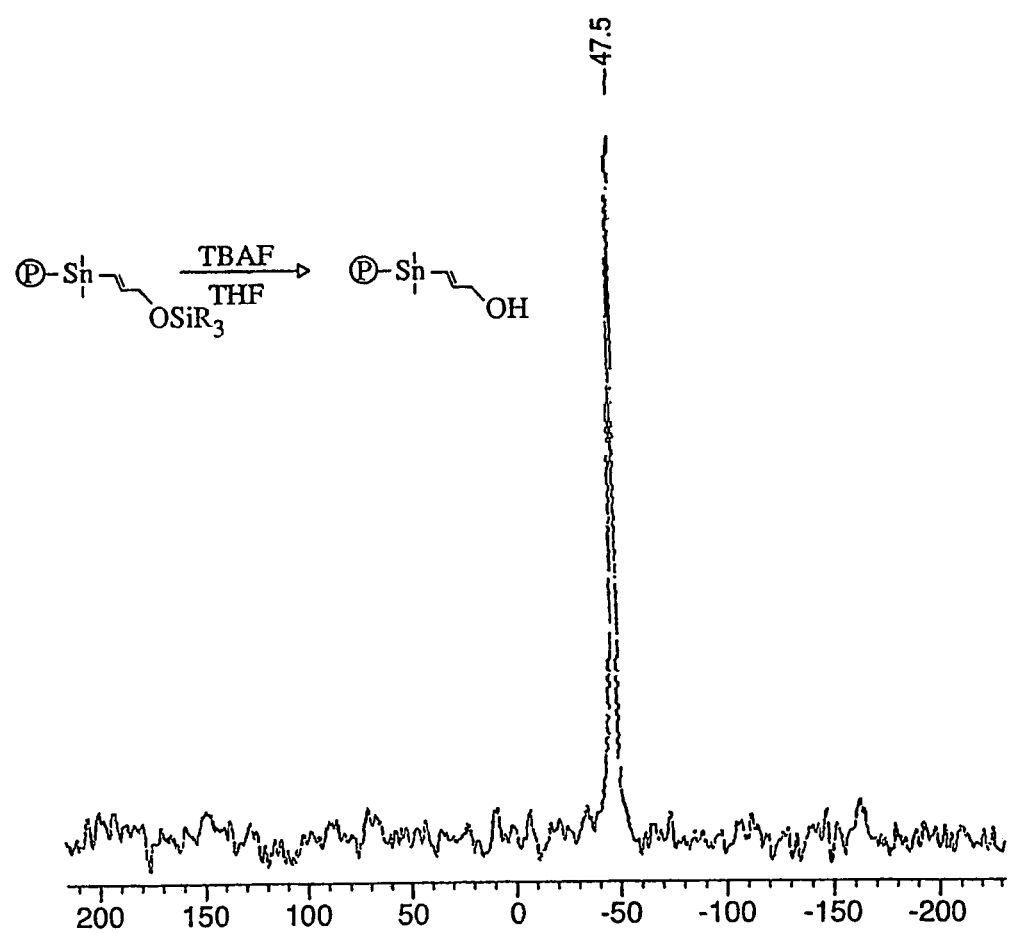
FIG. 9 depicts a $^{119}$Sn NMR spectrum of a polymer-bound propenylstannane.
Figure 10:
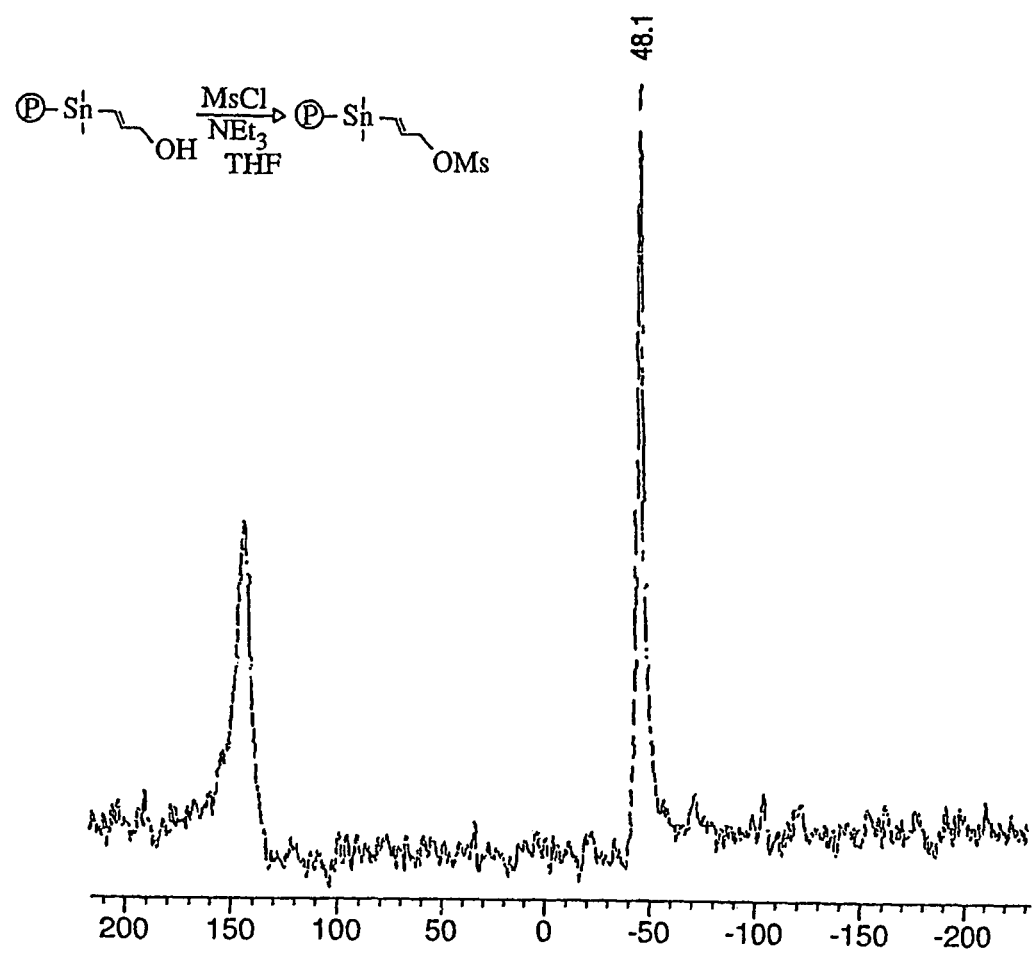
FIG. 10 depicts a $^{119}$Sn NMR spectrum of a polymer-bound propenylstannane.
Figure 11:
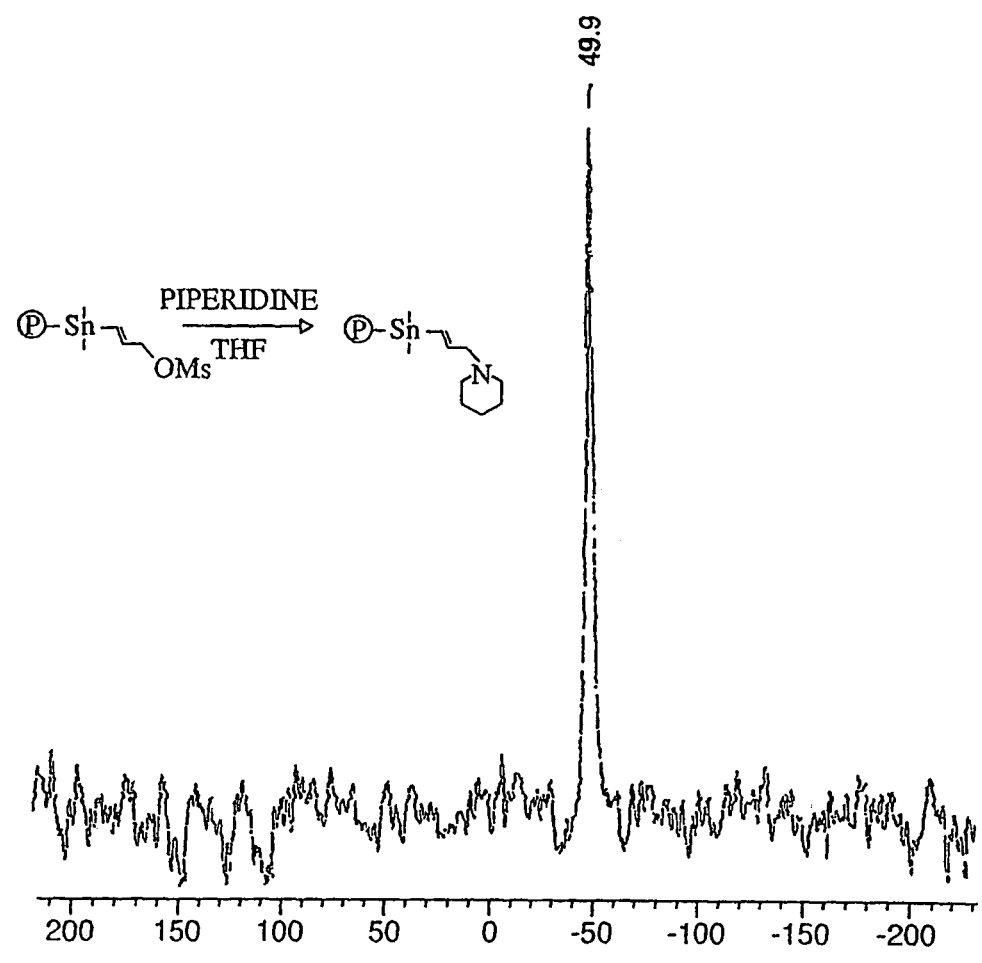
FIG. 11 depicts a $^{119}$Sn NMR spectrum of a polymer-bound propenylstannane.
Figure 12:
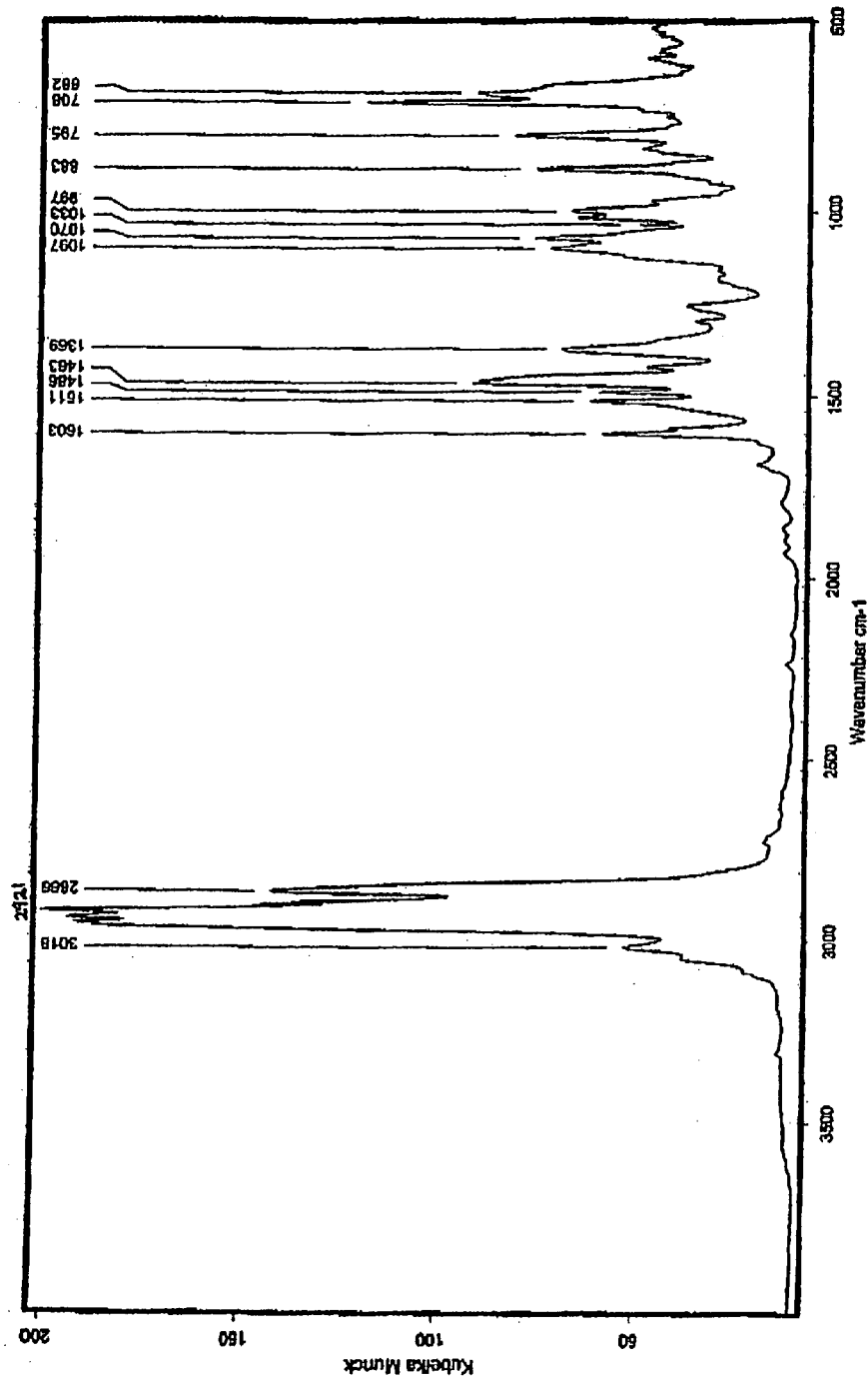
FIG. 12 depicts an IR spectrum of a polymer-bound propenylstannane.
Figure 13:
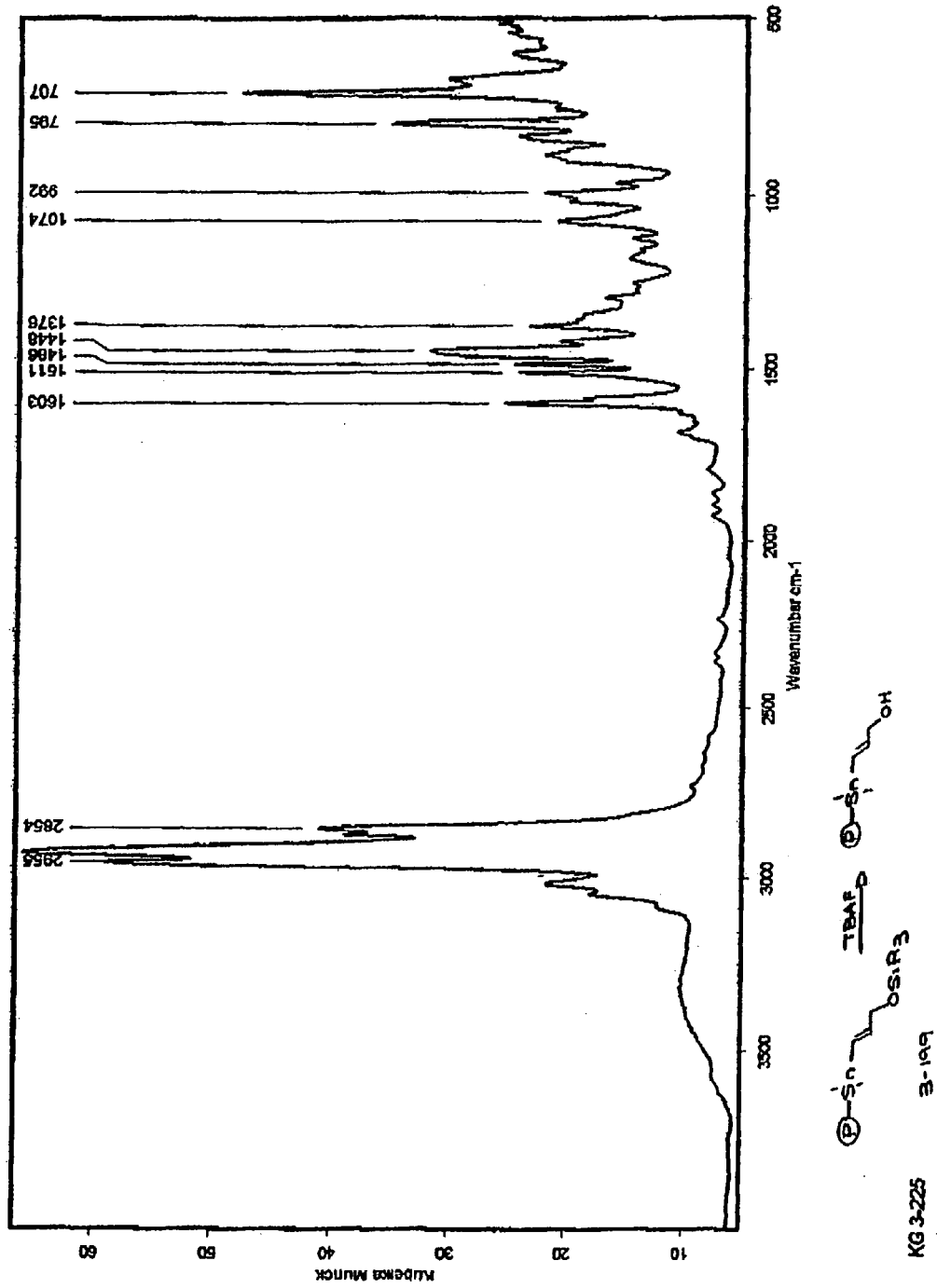
FIG. 13 depicts an IR spectrum of a polymer-bound propenylstannane.
Figure 14:
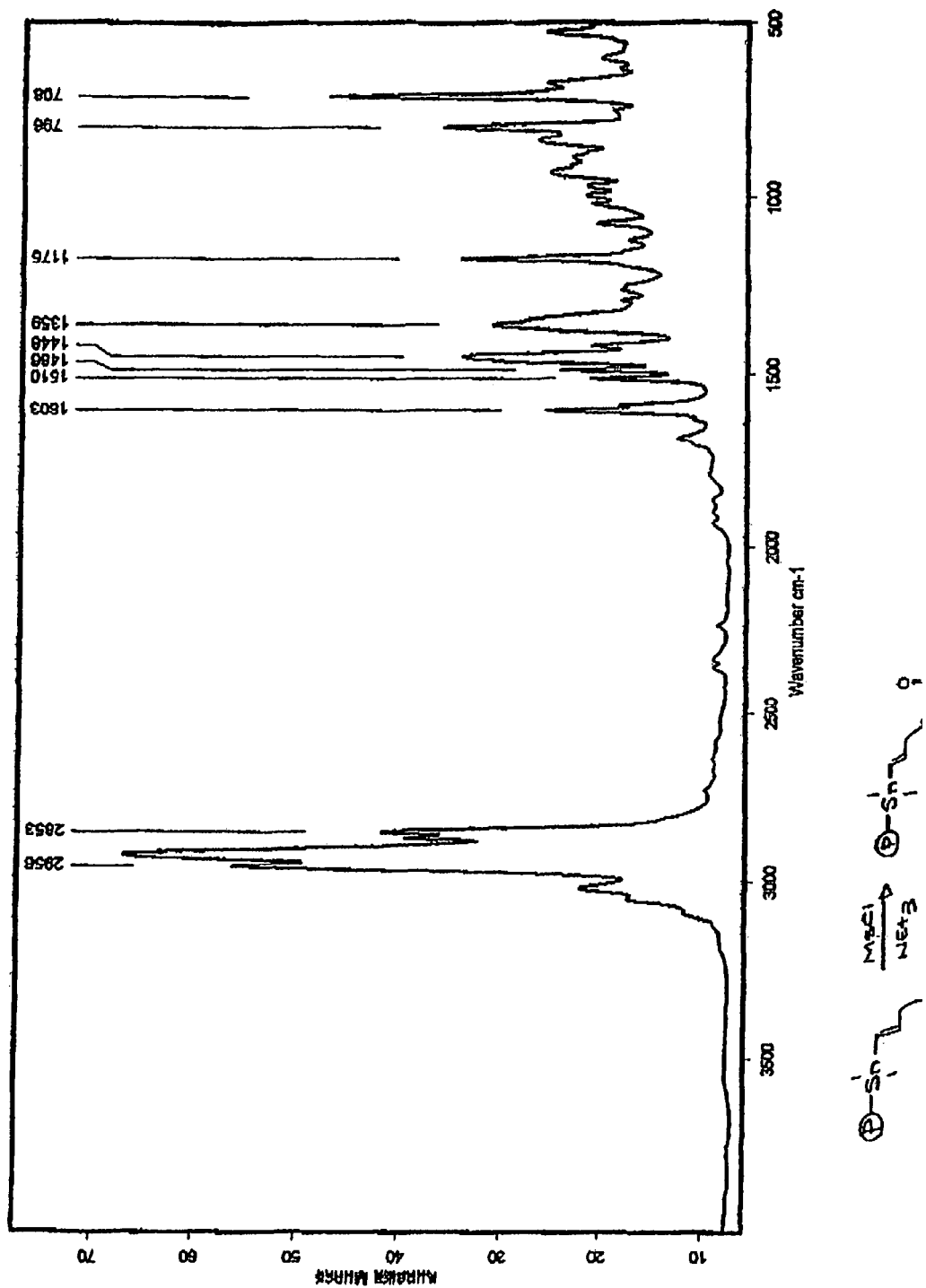
FIG. 14 depicts an IR spectrum of a polymer-bound propenylstannane.
Figure 15:
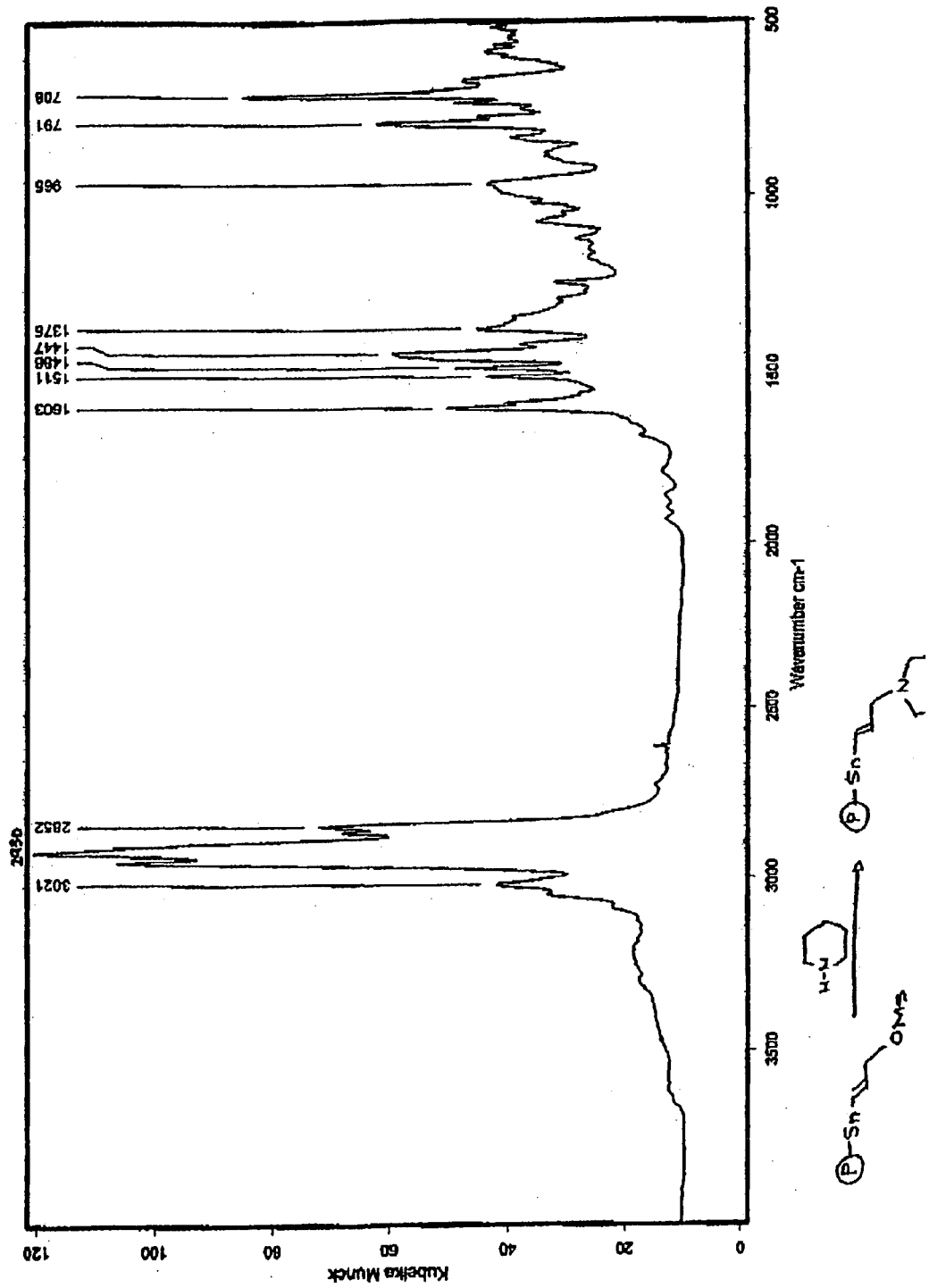
FIG. 15 depicts an IR spectrum of a polymer-bound propenylstannane.

Certain compounds of the present invention are precursors for the rapid and efficient radiolabeling of compounds. The precursor compounds of the invention are stable and may be stored for extended periods of time. The development of stable precursors to radiolabeled compounds is an important attribute of the present invention because radiolabeled compounds can have a very short shelf-life. The shelf-life of a compound is particularly important for radiopharmaceutical agents because degradation products formed during storage may be harmful to the patient. Thus, the present invention provides a solution to storing radiopharmaceutical agents. The present invention provides precursors to radiopharmaceutical agents that can be stored for extended periods of time and then easily converted to the radiopharmaceutical agent just prior to administration of the drug.

Hence, the present invention provides a method for preparing stable precursors to radioactive compounds. In addition, the present invention provides improved methods for synthesizing isotopically pure radiolabeled compounds without unwanted impurities. A prosthetic group has been designed that is attached to a polymer as a trialkylvinylstannane or trialkylarylstannane, facilitating removal of any unwanted impurities by filtration of the polymer by-product.

The invention relates generally to a method of using prosthetic groups to prepare radiophamaceutical compounds. One aspect of the present invention relates to a polymer-bound alkenylstannane containing a leaving group that can be displaced by a nucleophile. This prosthetic group allows for the derivatization of a wide variety of nucleophilic functional groups. In certain embodiments, the leaving group is an allylic or benzylic methanesulfonate. This procedure is advantageous because any impurities can simply be washed away from the solid support. Then, the molecule containing the prosthetic group is cleaved from the solid support using a process that simultaneously installs the radioisotope. Another aspect of the present invention relates to a polymer-bound alkenylstannane that contains an amino functional group. In certain preferred embodiments, the amino functional group is a piperidine ring.

Another aspect of the present invention relates to a method for preparing a polymer-bound prosthetic group comprising attaching an alkene to the surface of a polymer by an alkene-tin bond. This result is accomplished by reacting an alkenyl lithium reagent with dibutyl tin chloride that is bound to a polymeric surface, e.g., polystyrene. The leaving group of the prosthetic group is subsequently unmasked to avoid any unwanted side reactions during attachment of the prosthetic group to the solid support. In a preferred embodiment, the leaving group is a mesylate.

The leaving group or a precursor to the leaving group can be protected using any protecting group that is stable to the reaction conditions in which the alkenyl lithium reagent is reacted with the polymer-bound dibutyltin chloride. A large number of protecting groups are known in the art and are amenable to the present invention. Representative hydroxyl protecting groups are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991. Examples of hydroxyl protecting groups include t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, and the like.

Another aspect of the present invention relates to a method of preparing a radiopharmaceutical compound from a functionalized prosthetic group comprising the step of mixing a radioisotope, oxidant, and functionalized prosthetic group. In preferred embodiments, the radioisotope is $^{113}$I or $^{211}$At, and the oxidant is chloramine-T in ethanol/water.

The methods of the present invention are useful for the synthesis of compounds for treatment of numerous ailments, conditions, and diseases that afflict mammals, including cancer. The synthetic methods of the present invention are also useful for preparing compounds used in medical and biological imaging. An additional aspect of the present invention relates to the synthesis of combinatorial libraries of precursors of radiolabeled compounds. A further aspect of this invention relates to a kit comprising a precursor compound.
Preparation of Polymer-Supported Prosthetic Group The general objective is to develop a polymer-supported prosthetic group (Polymer C) for the radiolabelling of amines and other appended functionality. The initial plan is to prepare several polymer-supported radioiodopiperidine precursors and to use these precursors for the preparation of the desired radiolabeled compounds, e.g., radioiodopiperidines.

The general scheme for the production of Polymer C and its conversion to the polymer-supported piperidine (Polymer D) is outlined in Scheme 1. The polymer-supported protected alcohol (Polymer A) was prepared from the corresponding chlorostannane polymer through an organolithium intermediate. Polymer A was deprotected using TBAF to give the alcohol (Polymer B), which was then converted to the mesylate (Polymer C). Conversion to Polymer D proved to be straightforward.

Scheme 1

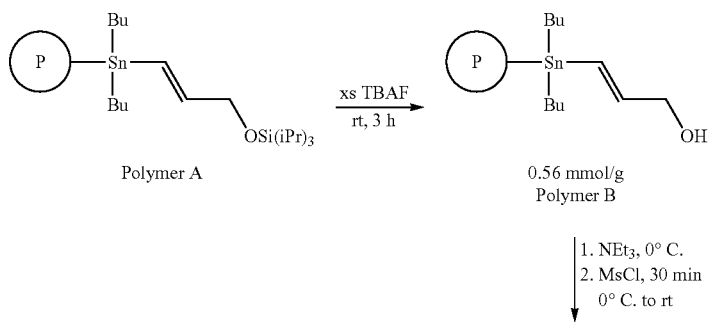

-continued

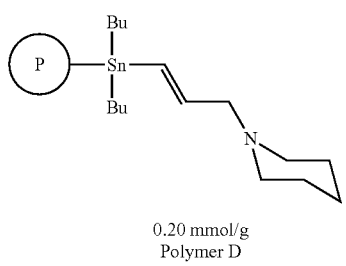

0.20 mmol/g
Polymer D

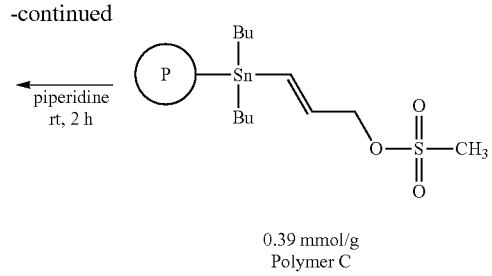

0.39 mmol/g
Polymer C

Based on HPLC analysis of the products of iododestannylation using $I_2$, the loading of these polymers was found to decrease with each step in the conversion. Starting from a chlorostannane polymer with a loading of 1.67 mmol of chloride per gram of polymer the desired prosthetic reagent, Polymer C had a loading capacity of 0.39 mmol/g. At each step in the conversion, $^{119}$Sn MAS NMR spectra showed only one tin signal at a position consistent with the anticipated chemical shift.

This methodology is advantageous, for example, because a wide range of nucleophiles are amenable to this procedure. For example, various substituted aliphatic amine nucleophiles could be used. Structural limitations of the nucleophile would include those functional groups that would promote elimination of the leaving group or attack on the tin atom. However, nitrogen, oxygen, sulfur, phosphorous, selenium, and arsenic nucleophiles could be used in the procedure described above. In addition, stabilized carbanions, e.g., enolates of malonates, ketones, and esters, are known to readily participate in nucleophilic displacement reactions at primary, allylic, and benzylic carbon centers.

After each step, the desired insoluble polymeric materials are washed several times with appropriate solvents to remove any excess reagents and unwanted by-products. In each case, the polymers have been characterized by spectroscopy ($^{119}$Sn MAS NMR and IR (DRIFT)) and by analyzing the products of iodinolysis.

The insoluble polymeric materials were analyzed in three ways: solid phase MAS $^{119}$Sn NMR spectroscopy and IR using a DRIFT attachment as well as by iodinolysis of the polymer. The products of the latter reaction, monitored by HPLC, allow for determination of the type and quantification of the amount of alkenyl or aromatic compounds attached to the polymer.

A large number of polymeric solid supports are known in the art and amenable to the present invention. The solid support should contain a functional group that is capable of bonding to a tin atom. Specifically, the solid support should have a functional group that is capable of forming a covalent bond to a dialkyltin halide. Representative examples of polymeric supports that could be used in the present invention are polystyrene, polyurethane, polyethylene glycol, poly(ethylene-co-vinyl acetate), polyethylene, polystyrene/rubber, or poly(ethylene-co-propylene), agarose, polyacrylamide, polyacrylate, polyamide, polyethyleneoxy, or copolymers and grafts of such. Other embodiments of solid-supports include small particles, non-porous surfaces, addressable arrays, etc. In certain aspects, the solid support is a controlled-pore-glass (CPG) support, such as the CPG supports commercially available from Millipore, silica beads, or silica wafers. In a preferred embodiment, the polymeric support is polystyrene, polyurethane, poly(ethylene-co-vinyl acetate), polyethylene, polystyrene/rubber, or poly(ethylene-co-propylene).

Radioisotopes Used in Medical Applications

Radioisotopes have been used in medication applications wherein radiation is used to treat disease or provide information about the functioning of a person's specific organs. In many cases, the information is used by physicians to make a quick, accurate diagnosis of the patient's illness. A wide variety of radioisotopes have been used in medical applications. Technetium-99m is used to image the skeleton and heart muscle in particular, but also for brain, thyroid, lungs (perfusion and ventilation), liver, spleen, kidney (structure and filtration rate), gall bladder, bone marrow, salivary and lacrimal glands, heart blood pool, infection and numerous specialized medical studies. Chromium-51 is used to label red blood cells and quantify gastro-intestinal protein loss. Cobalt-60 has found application in external beam radiotherapy. Copper-64 can be used to study genetic diseases affecting copper metabolism, such as Wilson's and Menke's diseases. Dysprosium-165 is used as an aggregated hydroxide for synovectomy treatment of arthritis. Ytterbium-169 can be used for cerebrospinal fluid studies in the brain. Iodine-125 has been used in cancer brachytherapy (prostate and brain), to evaluate the filtration rate of kidneys, and to diagnose deep vein thrombosis in the leg. It is also widely used in radioimmuno assays to show the presence of hormones in tiny quantities. Iodine-131 is widely used in treating thyroid cancer and in imaging the thyroid, and in diagnosis of abnormal liver function, renal (kidney) blood flow and urinary tract obstruction. A strong gamma emitter, but used for beta therapy, Iridium-192 is supplied in wire form for use as an internal radiotherapy source for cancer treatment. Iron-59 is used in studies of iron metabolism in the spleen. Phosphorus-32 (beta emitter) is used in the treatment of polycythemia vera (excess red blood cells). Potassium-42 is used for the determination of exchangeable potassium in coronary blood flow. Rhenium-188 (derived from Tungsten-188) is used to beta irradiate coronary arteries from an angioplasty balloon. Samarium-153, sold as Quadramet, is very effective in relieving the pain of secondary cancers lodged in the bone. Also very effective for prostate and breast cancer, Selenium-75 is used in the form of seleno-methionine to study the production of digestive enzymes. Sodium-24 is used for studies of electrolytes within the body. Strontium-89 has been found to be very effective in reducing the pain of prostate cancer. Xenon-133 and Xenon-127 are used for pulmonary (lung) ventilation studies. Yttrium-90 which emits beta-particles has been used for cancer therapy and as silicate colloid for the treatment of arthritis in larger joints. Radioisotopes of palladium, cesium, gold and ruthenium are used in brachytherapy. Astatine-211 is an alpha-emitter that has been used to treat lung cancer in mice and is currently being investigated for treatment of brain cancer in humans. See S. J. Kennel et al. *Radiation Research* 2002, 157, 633-641. Astatine-211 has been shown to be up to 1000 times more effective in eradicating cancer cells than I-131.

Some elements have multiple radioactive isotopes. One example is iodine, an element essential for health; insufficient iodine in one's diet can lead to a goiter. Iodine also is one of the earliest elements whose radioisotopes were used in what is now called nuclear medicine. The most common, stable form of iodine has an atomic number of 53 (protons) and a mass number of 127 (53 protons plus 74 neutrons). Because its nucleus has the "correct" number of neutrons, it is stable and is not radioactive. A less stable form of iodine also has 53 protons, but four extra neutrons, for a total atomic weight of 131 (53 protons and 78 neutrons). With "too many" neutrons in its nucleus, it is unstable and radioactive, with a half-life of eight days. Because it behaves chemically as iodine, it travels throughout the body and localizes in the thyroid gland just like the stable form of iodine. However, because it is radioactive, its presence can be detected. Consequently, iodine-131 became one of the earliest radioactive tracers.

Diagnostic Radiopharmaceuticals

Diagnostic techniques in nuclear medicine use radioactive tracers which emit gamma-rays from within the body. These tracers are generally short-lived isotopes linked to chemical compounds which permit specific physiological processes to be scrutinized. They can be given by injection, inhalation or orally. The first type are where single photons are detected by a gamma camera which can view organs from many different angles. The camera builds up an image from the points from which radiation is emitted; this image is enhanced by a computer and viewed by a physician on a monitor for indications of abnormal conditions.

A more recent development is Positron Emission Tomography (PET) which is a more precise and sophisticated technique using isotopes produced in a cyclotron. A positron-emitting radionuclide is introduced usually by injection, and accumulates in the target tissue. As it decays it emits a positron, which promptly combines with a nearby electron resulting in the simultaneous emission of two identifiable gamma rays in opposite directions. These are detected by a PET camera and give very precise indication of their origin. PET's most important clinical role is in oncology, with fluorine-18 as the tracer, since it has proven to be the most accurate non-invasive method of detecting and evaluating most cancers. It is also used in cardiac and brain imaging.

The ability to position the radiation source within the body marks the fundamental difference between nuclear medicine imaging and other imaging techniques, such as x-rays. Gamma imaging by either method described provides a view of the position and concentration of the radioisotope within the body. Organ malfunction can be indicated if the isotope is either partially taken up in the organ (cold spot), or taken up in excess (hot spot). If a series of images is taken over a period of time, an unusual pattern or rate of isotope movement could indicate malfunction in the organ.

A distinct advantage of nuclear imaging over x-ray techniques is that both bone and soft tissue can be imaged very successfully. This has led to its common use in developed countries where the probability of anyone having such a test is about one in two and rising.

Every organ in our bodies acts differently from a chemical point of view. Doctors and chemists have identified a number of chemicals which are absorbed by specific organs. The thyroid, for example, takes up iodine, the brain consumes quantities of glucose, and so on. With this knowledge, radiopharmacists are able to attach various radioisotopes to biologically active substances. Once a radioactive form of one of these substances enters the body, it is incorporated into the normal biological processes and excreted in the usual ways.

Diagnostic radiopharmaceuticals have been used to examine blood flow to the brain, functioning of the liver, lungs, heart or kidneys, to assess bone growth, and to confirm other diagnostic procedures. Another important use is to predict the effects of surgery and assess changes since treatment.

A radioisotope used for diagnosis must emit gamma rays of sufficient energy to escape from the body and it must have a half-life short enough for it to decay away soon after imaging is completed. The radioisotope most widely used in medicine is technetium-99m, employed in some 80% of all nuclear medicine procedures. It is an isotope of the artificially-produced element technetium and it has almost ideal characteristics for a nuclear medicine scan.

Preparation of Radiopharmaceutical Compound

A radiopharmaceutical compound can be prepared from a prosthetic group by mixing a radioisotope, an oxidant, and the functionalized polymer-bound prosthetic group. The oxidant may be chloramine-T in ethanol/water with or without acetic acid, N-chlorosuccinimide with acetic acid in methanol, tert-butylhydroperoxide with acetic acid in chloroform, Iodogen with a phosphate buffer, or iodobeads with or without acetic acid in methanol. In addition, the oxidant can be dichloramine-T, chloramine-B, a peracid (e.g., peracetic acid or perbenzoic acid), or 1,3,4,6-tetrachloro-3α,6α-diphenylglycoluril. A variety of radioisotopes are amenable to the present invention. Representative examples of radioisotopes that can be used in the present invention include a radioisotope of fluorine, carbon, bromine, astatine, or iodine. In preferred embodiments, the radioisotope is $^{18}$F, $^{11}$C, $^{76}$Br, $^{211}$At, $^{123}$I, $^{131}$I or $^{125}$I. The various radioisotopes can be prepared using procedures known in the art.

The methods of the invention maintain the advantages of rapid and clean reaction, but also offer a solution to the purification problem. Treatment of the insoluble polymer-bound compounds of the instant invention, with a radioisotope and an oxidant, releases radiolabeled compounds into solution while any excess precursor and the insoluble polymeric side-product may be removed by filtration. Thus simple and rapid filtration will result in chemically pure material. In certain embodiments, the radiopharmaceutical compounds formed by this process can be produced at the no-carrier-added level and will have a specific activity as high as the source of radioisotope. This approach could produce the high specific activity radiopharmaceutical compound required for receptor specificity in a biological system, e.g., human body.

Combinatorial Libraries

The subject methods and compounds readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library may be created at a variety of different levels. For instance, the substrate used in a combinatorial approach can be diverse in terms of the core aryl or alkenyl moiety, e.g., a variation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

Multipin Synthesis

The libraries of the subject method can take the multipin library format. Briefly, Geysen and co-workers (Geysen et al. (1984) *PNAS* 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also be appended to the pins so that the compounds may be cleaved from the supports after synthesis for assessment of purity and further evaluation (c.f., Bray et al. (1990) *Tetrahedron Lett* 31:5811-5814; Valerio et al. (1991) *Anal Biochem* 197:168-177; Bray et al. (1991) *Tetrahedron Lett* 32:6163-6166).

Divide-Couple-Recombine

In yet another embodiment, a variegated library of compounds can be provided on a set of beads utilizing the strategy of divide-couple-recombine (see, e.g., Houghten (1985) *PNAS* 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271-280, Fodor, S. P. A. (1991) *Science* 251:767; Pirrung et al. (1992) U.S. Pat. No. 5,143,854; Jacobs et al. (1994) *Trends Biotechnol* 12:19-26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

Tagging with Sequenceable Bio-Oligomers

The principle of using oligonucleotides to encode combinatorial synthetic libraries was described in 1992 (Brenner et al. (1992) PNAS 89:5381-5383), and an example of such a library appeared the following year (Needles et al. (1993) PNAS 90:10700-10704). A combinatorial library of nominally $7^7$(=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In some embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529-2531), orthogonality in synthesis is achieved by employing acid-labile protection for the coding strand and base-labile protection for the compound strand.

In an alternative approach (Nikolaiev et al. (1993) Pept Res 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

Non-Sequenceable Tagging: Binary Encoding

An alternative form of encoding the test compound library employs a set of non-sequenceable electrophoric tagging molecules that are used as a binary code (Ohlmeyer et al. (1993) PNAS 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Kits

The invention provides for a kit in which precursor compounds of the present invention are used according to a method described herein to provide a desired radiolabeled compound for imaging or therapy. A kit comprises one or more of the compounds described above, in combination with a pharmaceutically acceptable carrier, such as sterile normal saline or human serum albumin. Other substances may also be used as carriers in accordance with this embodiment of the invention; for example, detergents, dilute alcohols, carbohydrates, auxiliary molecules, and the like. A kit of the invention may of course also contain such other items as may facilitate its use, such as syringes, instructions, buffers, reducing agents, reaction vials, and the like.

In one embodiment, a kit includes an oxidant or an oxidizing agent, and about 1 to about 30 mCi of the radionuclide-labeled imaging agent described above, in combination with a pharmaceutically acceptable carrier, for diagnostic or imaging use. In another embodiment, a kit includes an oxidant or an oxidizing agent, and about 10 to about 5000 mCi of the radionuclide-labeled imaging agent described above, in combination with a pharmaceutically acceptable carrier, for therapeutic use. The compounds of the present invention and the carrier may be provided in solution or in lyophilized form. When the compounds of the present invention and carrier of a kit are in lyophilized form, the kit may optionally contain a sterile and physiologically acceptable reconstitution medium, such as water, saline, buffered saline, and the like.

In another embodiment, a kit of the invention includes a filter or filtration device to remove excess precursor-compound or the insoluble polymeric side product.

In another embodiment, a kit of the invention may produce or contain precursor compounds that have been covalently or non-covalently combined with a chelating agent; an auxiliary molecule, such as mannitol, gluconate, glucoheptonate, tartrate, and the like; and a reducing agent, such as $SnCl_2$, Na dithionite or tin tartrate. The precursor compound/chelating agent and the auxiliary molecule may be present as separate components of the kit or they may be combined into a single kit component. The unlabeled precursor compound/chelating agent, the auxiliary molecule, and the reducing agent may be provided in solution or in lyophilized form, and these components of the kit may optionally contain stabilizers, such as NaCl, silicate, phosphate buffers, ascorbic acid, gentisic acid and the like. Additional stabilization of kit components may be provided; for example, by providing the reducing agent in an oxidation-resistant form.

DEFINITIONS

The term "antibody" includes molecules consisting of polypeptide chains. It includes antibody fragments and antigen binding domain fragments, monoclonal antibodies, and immunoglobulins.

The terms "nucleotide" and "nucleoside" include nucleotides and nucleosides with base components of either purine or pyrimidine. Examples of nucleotides and nucleosides include adenosine, guanosine, cytidine, uridine, deoxyadenosine, deoxyguanosine, deoxycytidine, deoxythymidine, adenylate, guanylate, cytidylate, uridylate, deoxyadenylate, deoxyguanylate, deoxycytidylate, and thymidylate.

A polymer is any relatively high molecular weight molecule, the structure of which comprises the multiple repetition of units derived, actually or conceptually, from molecules of low relative molecular mass. A polymer which is part of a larger molecule is relatively inert to any reactivity of the other functional groups of the molecule. An insoluble polymer may be removed or separated by filtration.

The term "peptide" refers to an oligomer in which the monomers are amino acids (usually alpha-amino acids) joined together through amide bonds. Peptides are two or more amino acid monomers long, but more often are between 5 to 10 amino acid monomers long and may be even longer, i.e., up to 20 amino acids or more, and peptides longer than 20 amino acids are contemplated. Peptides include peptide hormones, peptide mimetics, conformationally restricted peptides, and peptide analogues.

The term "protein" is well known in the art and usually refers to a very large polypeptide, or set of associated homologous or heterologous polypeptides, that has some biological function. For purposes of the present invention the terms "polypeptide" and "protein" are largely interchangeable.

The term "isotopically pure" means that the element, compound, or composition contains a greater proportion of one isotope in relation to other isotopes. In certain embodiments, the element, compound, or composition is greater than about 40%, 50%, or 60% isotopically pure. In a preferred embodiment, the element, compound, or composition is greater tlhan about 70%, 80%, or 90% isotopically pure. In a more preferred embodiment, the element, compound, or composition is greater than about 95%, 98%, or 99% isotopically pure.

In general the abbreviations used herein for designating the amino acids and the protective groups are based on recommendations of the IUPAC-IUIB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compound may include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

A "radiolabel" refers to a molecule that is capable of generating a detectable image that may be detected either by the naked eye or using an appropriate techniques, e.g. positron emission tomography (PET), single photon emission tomography (SPECT) or magnetic resonance imaging (MRI). Certain exemplary labels are radionuclides, or radioactive isotopes of an element. Examples of radionuclides include $^{123}$I, $^{99m}$Tc, $^{18}$F, $^{68}$Ga, $^{62}$Cu, $^{111}$In, $^{123}$I, $^{124}$I, $^{125}$I, $^{186}$Re, $^{188}$Re, $^{90}$Y, $^{212}$Bi $^{89}$Sr, $^{166}$Ho, $^{153}$Sm, $^{67}$Cu, $^{64}$Cu, $^{11}$C, $^{206}$At, $^{208}$At, $^{211}$At, $^{215}$At, $^{217}$At, $^{75}$Br, $^{77}$Br, $^{78}$Br, $^{80}$Br, $^{82}$Br, and $^{76}$Br. Additional labels are suitable for obtaining a magnetic resonance image (MRI), including unpaired spin atoms and free radicals (e.g. iron, lanthanides and gadolinium) and contrast agents (e.g. chelated DTPA manganese).

The term "solid support" includes insoluble, functionalized, polymeric materials to which library members or reagents may be attached, with or without a linker, allowing them to be readily separated, for example by filtration, centrifugation, from, for example, excess reagents, soluble reaction by-products, or solvents.

The term "OMEM" refers to a oxygen atom that is bonded to a methoxyethoxymethyl group.

The term "heteroatom" as used herein means an atom of any element other than carbon or hydrogen. Exemplary heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251-259. The Hammett constant values are generally negative for electron donating groups (σ[P]=−0.66 for $NH_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In one embodiment, a straight chain or branched chain alkyl has 30 or fewer carbon atoms in its backbone (e.g., $C_1$-$C_{30}$ for straight chain, $C_3$-$C_{30}$ for branched chain), and in another embodiment, 20 or fewer. Likewise, exemplary cycloalkyls have from 3-10 carbon atoms in their ring structure, and in another embodiment, have 5, 6 or 7 carbons in the ring structure.

Unless the number of carbons is otherwise specified, "lower alkyl" as used herein means an alkyl group, as defined above, but having from one to ten carbons, and in one embodiment, from one to six carbon atoms in its backbone structure. Likewise, "lower alkenyl" and "lower alkynyl" have similar chain lengths. In one embodiment, alkyl groups are lower alkyls. In one embodiment, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

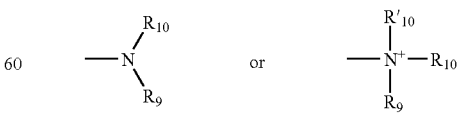

wherein $R_9$, $R_{10}$ and $R'_{10}$ each independently represent a group permitted by the rules of valence.

The term "acylamino" is art-recognized and refers to a moiety that can be represented by the general formula:

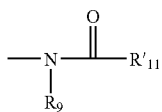

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

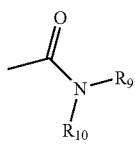

wherein $R_9$, $R_{10}$ are as defined above. In one embodiments, of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

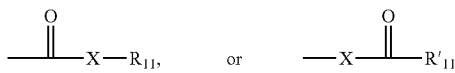

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

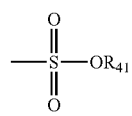

in which $R_{41}$ is an electron pair, hydrogen, alkyl, cycloalkyl, or aryl.

The term "malonate" is art recognized and includes a moiety that can be represented by the general formula:

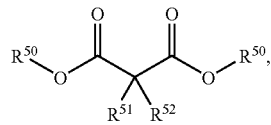

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "β-ketoester" is art recognized and includes a moiety that can be represented by the general formula:

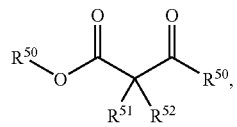

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-nitroester" is art recognized and includes a moiety that can be represented by the general formula:

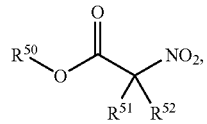

wherein $R^{50}$ is alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-cyanoester" is art recognized and includes a moiety that can be represented by the general formula:

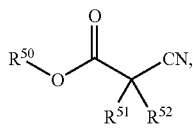

wherein $R^{50}$ is alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-phosphonoester" is art recognized and includes a moiety that can be represented by the general formula:

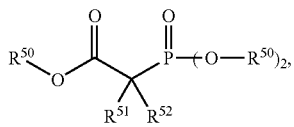

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The term "α-ketophosphonate" is art recognized and includes a moiety that can be represented by the general formula:

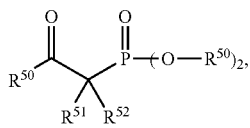

wherein $R^{50}$ represents independently for each occurrence alkyl, cycloalkyl, heterocycloalkyl, aryl, or aralkyl; $R^{51}$ is H, alkyl, cycloalkyl, heterocycloalkyl, aryl, or aralkyl; and $R^{52}$ is a radical, H, alkyl, cycloalkyl, heterocycloalkyl, aryl, or aralkyl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

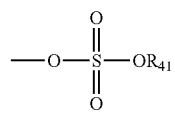

in which $R_{41}$ is as defined above.

The term "sulfonylamino" is art recognized and includes a moiety that can be represented by the general formula:

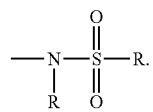

The term "sulfamoyl" is art-recognized and includes a moiety that can be represented by the general formula:

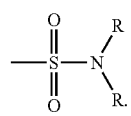

The term "sulfonyl", as used herein, refers to a moiety that can be represented by the general formula:

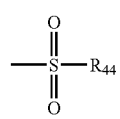

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

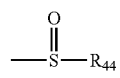

in which $R_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as precursors), wherein one or more simple variations of substituents are made which do not adversely affect the efficacy of the compound to function as precursors of radiolabelled compounds. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

COMPOUND OF THE INVENTION

One aspect of the present invention relates to a compound represented by formula 1:

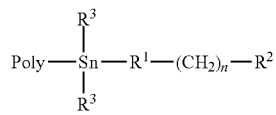

wherein

Poly represents a polymer;

$R^1$ represents alkenyl, aryl, heteroaryl, alkynyl, or aralkyl;

$R^2$ represents —$NR^4R^5$, phosphate, phosphite, phosphine, $XR^5$, Z, halide, or sulfonate;

X is O, S, Se, or $AsR^5$;

Z is a malonate, β-ketoester, α-nitroester, α-cyanoester, or α-phosphonoester, or α-ketophosphonate;

n is 1-15;

$R^3$ represents independently for each occurrence alkyl, aralkyl, alkenyl or alkynyl; and $R^4$ and $R^5$ represent independently for each occurrence hydrogen, alkyl, heteroalkyl, cycloalkyl, heterocycloalkyl, alkenyl, alkynyl, aryl, heteroaryl, aralkyl, or heteroaralkyl; or there is a covalent bond between $R^4$ and $R^5$ in an instance of —$NR^4R^5$.

In certain embodiments, the compounds of the present invention are represented by formula 1, wherein n is 1-5.

In certain embodiments, the compounds of the present invention are represented by formula 1, wherein n is 1.

In certain embodiments, the compounds of the present invention are represented by formula 1, wherein $R^1$ is alkenyl or aryl.

In certain embodiments, the compounds of the present invention are represented by formula 1, wherein $R^1$ is alkenyl.

In certain embodiments, the compounds of the present invention are represented by formula 1, wherein $R^1$ is —[$CR^8$=$CR^8$]$_w$—, wherein $R^8$ represents independently for each occurrence H, halogen, alkyl, aryl, or aralkyl; and w is 1, 2, or 3.

In certain embodiments, the compounds of the present invention are represented by formula 1, wherein $R^1$ is —CH=CH—.

In certain embodiments, the compounds of the present invention are represented by formula 1, wherein $R^2$ is a halide or sulfonate.

In certain embodiments, the compounds of the present invention are represented by formula 1, wherein $R^2$ is a sulfonate.

In certain embodiments, the compounds of the present invention are represented by formula 1, wherein $R^2$ is mesylate or tosylate.

In certain embodiments, the compounds of the present invention are represented by formula 1, wherein $R^3$ is alkyl.

In certain embodiments, the compounds of the present invention are represented by formula 1, wherein $R^3$ is n-butyl.

In certain embodiments, the compounds of the present invention are represented by formula 1, wherein $R^1$ is —HC=CH—, $R^3$ is alkyl, n is 1, poly is polystyrene, and $R^2$ is mesylate or tosylate.

In certain embodiments, the compounds of the present invention are represented by formula 1, wherein $R^1$ is —HC=CH—, $R^3$ is alkyl, n is 1, poly is polystyrene, and $R^2$ is —$NR^4R^5$.

In certain embodiments, the compounds of the present invention are represented by formula 1, wherein $R^2$ is —$NR^4R^5$ or $XR^5$.

In certain embodiments, the compounds of the present invention are represented by formula 1, wherein $R^2$ is $-NR^4R^5$.

In certain embodiments, the compounds of the present invention are represented by formula 1, wherein $R^2$ is an amino group of a nucleotide, nucleoside, nucleic acid, carbohydrate (monomer or polymer), purine, pyrimide, or amino acid.

In certain embodiments, the compounds of the present invention are represented by formula 1, wherein $R^2$ is optionally substituted optionally substituted 1-piperidinyl.

In certain embodiments, the compounds of the present invention are represented by formula 1, wherein $R^1$ is $-HC=CH-$, $R^3$ is alkyl, n is 1, said polymer is polystyrene, and $R^2$ is optionally substituted 1-piperidinyl.

In certain embodiments, the compounds of the present invention are represented by formula 1, wherein $R^2$ is $-XR^5$, wherein X is O or S.

In certain embodiments, the polymer of structure 1 is functionalized by the moiety $-Sn(R^3)_2R^1(CH_2)_nR^2$ on a plurality of monomeric units of the polymer.

In certain embodiments, $R^2$ is an amino group of a peptide.

In certain embodiments, $R^2$ is an amino group of an antibody.

In certain embodiments, poly is a polyethylene glycol, polystyrene, polyamide, or polypeptide.

In certain embodiments, poly is polystyrene, polyurethane, poly(ethylene-co-vinyl acetate), polyethylene, polystyrene/rubber, or poly(ethylene-co-propylene).

In certain embodiments, poly is polystyrene.

In certain embodiments, the compounds of the present invention are represented by formula 1, wherein $R^2$ is represented by formula 2:

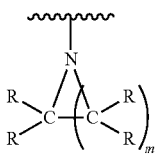

2 wherein m is 1-8; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, $-COR^6$, $-CO_2R^6$, $-C(O)N(R^6)_2$, $-N(R^6)C(O)R^6$, $-OC(O)N(R^6)_2$, $-N(R^6)CO_2R^7$, $-C(S)N(R^6)_2$, $-N(R^6)C(S)R^6$, $-OC(S)N(R^6)_2$, $-N(R^6)C(S)OR^7$, $-N(R^6)C(O)N(R^6)_2$, $-N(R^6)C(S)N(R^6)_2$, or $-(CH_2)_q-R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; and $R^7$ represents independently for each occurrence alkyl, alkenyl, aryl, or aralkyl.

In certain embodiments, the compounds of the present invention are represented by formula 1, wherein $R^2$ is represented by formula 2:

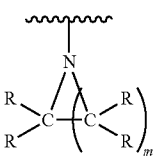

2 wherein m is 3 or 4; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, $-COR^6$, $-CO_2R^6$, $-C(O)N(R^6)_2$, $-N(R^6)C(O)R^6$, $-OC(O)N(R^6)_2$, $-N(R^6)CO_2R^7$, $-C(S)N(R^6)_2$, $-N(R^6)C(S)R^6$, $-OC(S)N(R^6)_2$, $-N(R^6)C(S)OR^7$, $-N(R^6)C(O)N(R^6)_2$, $-N(R^6)C(S)N(R^6)_2$, or $-(CH_2)_q-R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; $R^7$ represents independently for each occurrence alkyl, alkenyl, aryl, or aralkyl; and poly is polystyrene.

Methods for Preparing Polymer-Bound Prosthetic Groups

Another aspect of the present invention relates to a method of synthesizing a polymer-bound prosthetic group, comprising the steps of:

combining a first compound and a polymer to give a first polymer-bound compound; and combining a second compound with said first polymer-bound compound to give a second polymer-bound compound comprising a functionalized prosthetic group, wherein said second compound is an amine, phosphate, phosphite, phosphine, alcohol, phenol, thiol, alkylselenide, arylselenide, bis(alkyl)arsenide, bis(aryl)arsenide, malonate, β-ketoester, α-nitroester, α-cyanoester, α-phosphonoester, or α-ketophosphonate, or an anion derived from any of them; said polymer comprises a tin chloride moiety; and said first compound is represented by formula 3:

$$M\text{-}R^1\text{---}(CH_2)_n\text{---}R^2 \qquad 3$$

wherein
M is a cation;
$R^1$ represents alkenyl, aryl, heteroaryl, alkynyl, or aralkyl;
$R^2$ is $OSi(alkyl)_3$, OMEM, acyloxy, or OBn; and
n is 1-15.

In certain embodiments, the present invention relates to the aforementioned method, wherein n is 1-5.

In certain embodiments, the present invention relates to the aforementioned method, wherein n is 1.

In certain embodiments, the present invention relates to the aforementioned method, wherein M is an alkali metal cation or alkaline earth metal cation.

In certain embodiments, the present invention relates to the aforementioned method, wherein M is Li, Na, K, ZnCl, ZnBr, MgBr, or MgCl.

In certain embodiments, the present invention relates to the aforementioned method, wherein $R^2$ is $OSi(alkyl)_3$.

In certain embodiments, the present invention relates to the aforementioned method, wherein $R^2$ is $OSi(iPr)_3$.

In certain embodiments, the present invention relates to the aforementioned method, wherein $R^1$ is alkenyl or aryl.

In certain embodiments, the present invention relates to the aforementioned method, wherein $R^1$ is alkenyl.

In certain embodiments, the compounds of the present invention are represented by formula 1, wherein $R^1$ is $-[CR^8=CR^8]_w-$, wherein $R^8$ represents independently for each occurrence H, halogen, alkyl, aryl, or aralkyl; and w is 1, 2, or 3.

In certain embodiments, the present invention relates to the aforementioned method, wherein $R^1$ is $-CH=CH-$.

In certain embodiments, the present invention relates to the aforementioned method, wherein said second compound is an amine, alcohol, phenol, thiol, malonate, β-ketoester, or an anion derived from any of them.

In certain embodiments, the present invention relates to the aforementioned method, wherein said second compound is an amine, alcohol, or an anion derived from any of them.

In certain embodiments, the present invention relates to the aforementioned method, wherein said second compound is an amine or an anion derived therefrom.

In certain embodiments, the present invention relates to the aforementioned method, wherein said functionalized prosthetic group is represented by formula 2:

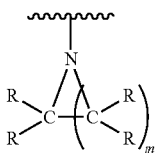

2 wherein m is 1-8; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, $-COR^6$, $-CO_2R^6$, $-C(O)N(R^6)_2$, $-N(R^6)C(O)R^6$, $-OC(O)N(R^6)_2$, $-N(R^6)CO_2R^7$, $-C(S)N(R^6)_2$, $-N(R^6)C(S)R^6$, $-OC(S)N(R^6)_2$, $-N(R^6)C(S)OR^7$, $-N(R^6)C(O)N(R^6)_2$, $-N(R^6)C(S)N(R^6)_2$, or $-(CH_2)_q-R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; and $R^7$ represents independently for each occurrence alkyl, alkenyl, aryl, or aralkyl.

In certain embodiments, the present invention relates to the aforementioned method, wherein said functionalized prosthetic group is represented by formula 2:

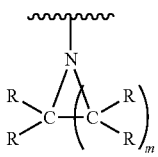

2 wherein m is 3 or 4; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, $-COR^6$, $-CO_2R^6$, $-C(O)N(R^6)_2$, $-N(R^6)C(O)R^6$, $-OC(O)N(R^6)_2$, $-N(R^6)CO_2R^7$, $-C(S)N(R^6)_2$, $-N(R^6)C(S)R^6$, $-OC(S)N(R^6)_2$, $-N(R^6)C(S)OR^7$, $-N(R^6)C(O)N(R^6)_2$, $-N(R^6)C(S)N(R^6)_2$, or $-(CH_2)_q-R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; and $R^7$ represents independently for each occurrence alkyl, alkenyl, aryl, or aralkyl.

In certain embodiments, the present invention relates to the aforementioned method, wherein said functionalized prosthetic group is optionally substituted 1-piperidinyl.

In certain embodiments, the present invention relates to the aforementioned method, wherein said polymer comprises a tin chloride moiety and polyethylene glycol, polystyrene, polyamide, or polypeptide.

In certain embodiments, the present invention relates to the aforementioned method, wherein said polymer comprises a tin chloride moiety and polystyrene, polyurethane, poly(ethylene-co-vinyl acetate), polyethylene, polystyrene/rubber, or poly(ethylene-co-propylene).

In certain embodiments, the present invention relates to the aforementioned method, wherein said polymer comprises a tin chloride moiety and polystyrene.

In certain embodiments, the present invention relates to the aforementioned method, wherein said polymer comprises a dibutyltin chloride moiety and polystyrene.

In certain embodiments, the present invention relates to the aforementioned method further comprising the steps of: removing a protecting group from $R^2$; and converting $R^2$ to a leaving group selected from the group consisting of halides and sulfonates.

Method for Preparing Radiopharmaceutical Compounds from a Prosthetic Group

Another aspect of the present invention relates to a method for preparing a radiopharmaceutical compound from a polymer-bound compound comprising a functionalized prosthetic group, comprising the steps of:

mixing a radioisotope, an oxidant, and a polymer-bound compound comprising a functionalized prosthetic group, wherein said polymer-bound compound comprising a functionalized prosthetic group is represented by formula 1:

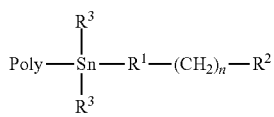

1 wherein
Poly represents a polymer;
$R^1$ represents alkenyl, aryl, heteroaryl, alkynyl, or aralkyl;
$R^2$ represents $-NR^4R^5$, $XR^5$, or Z;
X is O, S, Se, or $AsR^5$;
Z is a malonate, β-ketoester, α-nitroester, α-cyanoester, or α-phosphonoester, or α-ketophosphonate;
n is 1-15;
$R^3$ represents independently for each occurrence alkyl, aralkyl, alkenyl or alkynyl; and
$R^4$ and $R^5$ represent independently for each occurrence hydrogen, alkyl, heteroalkyl, cycloalkyl, heterocycloalkyl, alkenyl, alkynyl, aryl, heteroaryl, aralkyl, or heteroaralkyl; or there is a covalent bond between $R^4$ and $R^5$ in an instance of $-NR^4R^5$.

In certain embodiments, said oxidant is chloramine-T in ethanol/water with or without acetic acid, N-chlorosuccinimide with acetic acid in methanol, tert-butylhydroperoxide with acetic acid in chloroform, Iodogen with a phosphate buffer, iodobeads with or without acetic acid in methanol, dichloramine-T, chloramine-B, a peracid, or 1,3,4,6-tetrachloro-3α,6α-diphenylglycoluril In certain embodiments, said oxidant is chloramine-T in ethanol/water with or without acetic acid, N-chlorosuccinimide with acetic acid in methanol, tert-butylhydroperoxide with acetic acid in chloroform, Iodogen with a phosphate buffer, or iodobeads with or without acetic acid in methanol.

In certain embodiments, said radioisotope is $^{18}F$, $^{11}C$, $^{76}Br$, $^{211}At$, $^{123}I$, $^{131}I$ or $^{125}I$.

In certain embodiments, said radioisotope is $^{211}At$, $^{131}I$, $^{123}I$, or $^{18}F$.

In certain embodiments, said radioisotope is $^{211}At$.

In certain embodiments, said radioisotope is $^{131}I$.

In certain embodiments, said radiopharmaceutical compound formed by this process is produced at the no-carrier-added level and has a specific activity equal to about the specific activity level of the source of said radioisotope.

In certain embodiments, said radiopharmaceutical compound is isotopically pure.

In certain embodiments, said radiopharmaceutical compound is a radiolabeled peptide or protein; and said radiopharmaceutical compound is isotopically pure.

In certain embodiments, said radiopharmaceutical compound is a radiolabeled antibody; and said radiopharmaceutical compound is isotopically pure.

In certain embodiments, said radiopharmaceutical compound is a radiolabeled nucleotide or nucleoside; and said radiopharmaceutical compound is isotopically pure.

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that (his disclosure will be through and complete, and will fully convey the scope of the invention to those skilled in the art.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Coupling 2-Aminobenzophenone-Linker Complex to Solid Support

To a 30 mL peptide reaction flask was added 4-(4-(5-chloro-2-fluorenylmethoxycarbonylamino-benzoyl)-phenoxymethyl)phen oxyacetic acid (1.52 g, 2.4 mmol, 2.0 equivalents), aminomethyl resin (1.99 g, 1.19 mmol of 1% crosslinked divinylbenzene-styrene, 100 mesh size, substitution level 0.60 milliequivalents/g), and hydroxybenzotriazole monohydrate (0.808 g, 5.28 mmol, 4.4 equivalents). Anhydrous DMF (12 mL) was added to the flask and the mixture was vortexed for 0.5 hour to fully solvate the resin. Diisopropylcarbodiimide (808 mg, 5.28 mmol, 4.4 equivalents) was added by syringe. The reaction flask was stoppered and then vortexed for 24 hours at which point the ninhydrin test on approximately 10 mg of the solid support demonstrated that coupling was complete. The solvent and reagents were filtered away from the solid support and the support was rinsed five times with 20 mL DMF and five times with 20 mL $CH_2Cl_2$ (for each rinse the mixture was vortexed for at least 30 seconds before filtering off the solvent) and then dried in vacuo for 12 hours to give 5.

Coupling 2-Aminobenzophenone-Linker Complex to Solid Support

To a 30 mL peptide reaction flask was added 5 (2.0 g, 3.02 mmol, 2.0 equivalents), aminomethyl resin (1.91 g, 1.51 mmol of 1% crosslinked divinylbenzene-styrene, 200-400 mesh size, substitution level 0.79 milliequivalents/g), and hydroxybenzotriazole monohydrate (0.925 g, 6.04 mmol, 4.4 equivalents). Anhydrous DMF (10.4 mL) was added to the flask and the mixture was vortexed for 0.5 hour to fully solvate the resin. Diisopropylcarbodiimide (762 mg, 6.04 mmol, 4.4 equivalents) was added by syringe and an additional 2.0 mL of DMF was added to rinse down the sides of the peptide reaction flask. The reaction flask was stoppered and then vortexed for 24 hours at which point the ninhydrin test on approximately 10 mg of the solid support demonstrated that coupling was complete. The solvent and reagents were filtered away from the solid support and the support was rinsed five times with 20 mL DMF and five times with 20 mL $CH_2Cl_2$ (for each rinse the mixture was vortexed for at least 30 seconds before filtering off the solvent) and then dried in vacuo for 12 hours to give 6.

EXAMPLE 2

General Procedure for Preparation of Polymer-Bound Arylstannane

A protected haloarylaldehyde (1.5 mol equiv.) was added into a three-necked round-bottom flask, equipped with a T-bore stopcock, a rubber septum and a powder addition side arm containing of chlorostannane polymer (1.5 mol equiv. of SnCl). Under a flow of argon, freshly distilled dry THF was added by syringe. The flask and its contents were outgased three times at dry ice/acetone temperatures and an argon atmosphere was introduced. To the solution of haloarylaldehyde in THF at −78° C., n-butyllithium (1.3 mol equiv., 2.5 M) was added dropwise with the resultant formation of a yellow color. After 2 h at −78° C., the polymer was tipped into the THF solution, and the suspension was allowed to stir for 18 h and warm slowly to RT. Methanol was added to the suspension, and the suspension was filtered. The solid was washed with methanol, water, methanol/water/acetone, methanol/acetone and methanol several times.

Poly-(4S,5S)-2-(3-{dibutyl[2-(3- and 4-vinylphenyl) ethyl]stannyl}phenyl)-3,4-dimethyl-5-phenyl-1,3-oxazolidine)-co-divinylbenzene (9)

Protected 3-bromobenzaldehyde 7, (2.90 g, 8.7 mmol), was added into a three-necked 200 mL round-bottom flask, equipped with a T-bore stopcock, a rubber septum and a powder addition side arm containing 4.01 g of chlorostannane polymer 8 (~5.9 mmol of SnCl). Under a flow of argon, 80 mL of freshly distilled dry THF was added by syringe. The flask and its contents were outgased three times at dry ice/acetone temperatures and an argon atmosphere was introduced. To the solution of 7 in TEF at −78° C., n-butyllithium (3.0 mL, 7.5 mmol, 2.5 M) was added dropwise with the resultant formation of a yellow color. After 2 h at −78° C., the polymer was tipped into the THF solution, and the suspension was allowed to stir for 18 h and warm slowly to RT. Methanol (about 3 mL) was added to the suspension, and the suspension was filtered. The solid was washed with methanol, water, methanol/water/ acetone, methanol/acetone and methanol several times to yield 4.3 g of 9.

$^{119}$Sn MAS NMR: −42.1 ppm.

Poly-(4S,5S)-2-(4-{dibutyl[2-(3- and 4-vinylphenyl) ethyl]stannyl}phenyl)-3,4-dimethyl-5-phenyl-1,3-oxazolidine)-co-divinylbenzene (11)

1.02 g (3.1 mmol) of protected 4-bromobenzaldehyde 10, in 35 mL of THF, was reacted with 1.2 mL (3.0 mmol, 2.5 M) of n-butyllithium for 2 h at −78° C. Polymer 8, 1.05 g (~1.6 mmol of SnCl) was tipped into the THF solution, and the suspension was allowed to stir for 17 hrs. After addition of ~2 ml of methanol, the suspension was filtered and washed in the same manner as 9 to afford 1.24 g of 11.

IR (DRIFT, solid): ~1050 cm$^{-1}$ C—O stretch.

Poly-(3-{dibutyl[2-(3-and-4-vinylphenyl)ethyl] stannyl}benzaldehyde)-co-divinylbenzene (12)

The protected aryl-bound polymer 9 (3.98 g) was treated with a mixture of 25 mL of methanol, 9 mL of water and 25 mL of acetic acid by gentle shaking for 27 h. The solid was recovered by filtration and was washed successively with methanol, water, methanol/water/acetone, methanol/acetone, and methanol to yield 3.65 g of the aldehyde-bound polymer 12. Iodinolysis: 0.74 mmol of 3-iodobenzaldehyde per gram of polymer.

$^{119}$Sn MAS NMR: −39.0 ppm.

Poly-(4-{dibutyl[2-(3- and 4-vinylphenyl)ethyl] stannyl}benzaldehyde)-co-divinylbenzene (13)

1.22 g of the protected aryl-bound polymer 11, was treated with a mixture of 5 mL of methanol, 1.5 mL of water and 5 mL of acetic acid by shaking for 17 hrs. The solid was filtered and washed as before to yield 1.00 g of 13.

Iodinolysis: 0.78 mmol of 4-iodobenzaldehyde per gram of polymer

IR (DRIFT, solid): 1707 cm$^{-1}$ C=O, 2715 cm$^{-1}$ C$\underline{H}$O (weak)

Poly-(3-{dibutyl[2-(3-and-4-vinylphenyl)ethyl] stannyl}benzoic acid)-co-divinylbenzene (14)

The polymer-bound aldehyde 12 (190 mg, ~0.1 mmol of aldehyde), was added to a vial containing a solution of m-chloroperbenzoic acid (210 mg, 1.2 mmol) in 5 mL of methanol. After shaking for 25 h at RT, the solid was filtered and washed successively with 1 M NaOH, acetone, 1.7 M AcOH/ethanol, water, methanol/water/acetone, and methanol to afford 150 mg of 14. Iodinolysis: 0.33 mmol of 3-iodobenzoic acid per gram of polymer. $^{119}$Sn MAS NMR: −39.3 ppm.

Poly-(4-{dibutyl[2-(3- and 4-vinylphenyl)ethyl] stannyl}benzoic acid)-co-divinylbenzene (15)

980 mg of the polymer-bound aldehyde 13 was added to 1.44 g (8.3 mmol) of m-chloroperbenzoic acid in 20 mL of methanol. After shaking for 18 h at RT, the solid was filtered and washed with 1M NaOH/ethanol, 12 mM HCl/ethanol, ethanol/methanol/water/acetone, methanol to yield 980 mg of the acid bound polymer 15.

IR (DRIFT, solid): 1695 cm$^{-1}$ C=O. Iodinolysis: 0.66 mmol of 4-iodobenzoic acid per gram of polymer Poly-(4-{dibutyl[2-(3- and 4-vinylphenyl)ethyl] stannyl}hippuric acid)-co-divinylbenzene (16)

Into a 50 mL round-bottom flask, 44 mg (0.35 mmol) of glycine methyl ester hydrochloride, 45 mg (0.35 mmol) of diisopropylethylamine and 5 mL of dichloromethane were added and the mixture was stirred for few minutes to allow dissolution. To this was added 72 mg (0.35 mmol) of dicyclohexylcarbodiimide (DCC), 53 mg (0.34 mmol) of 1-hydroxybenzotriazide (1-HOBT) and 250 mg (~0.17 mmol) of the polymer-bound benzoic acid 15. After stirring under a flow of argon for 5 days, at RT, the solid was filtered and washed with methanol/acetone, dicholoromethane, and methanol.

The ester group was hydrolyzed at reflux in 10 mL THF/water (1:1) in the presence of NaOH (400 mg, 10 mmol) for 4 h. The solid was filtered and washed with 1 M HCl, water, methanol/water/acetone, methanol/acetone, methanol to yield 180 mg of the benzamide bound polymer 16. Iodinolysis: 0.58 mmol of 4-iodohippuric acid per gram of polymer Poly-(4-{dibutyl[2-(3- and 4-vinylphenyl)ethyl] stannyl}N,N-diethylethylenediamino benzamidyl)-co-divinylbenzene (17)

Into a 50 mL round-bottom flask were placed 28 mg (0.2 mmol) of diethylethylenediamine, 27 mg (0.2 mmol) of collidine, 61 mg (0.3 mmol) of dicyclohexylcarbodiimide (DCC), 32 mg (0.2 mmol) of 1-hydroxybenzotriazide (1-HOBT), 150 mg (~0.1 mmol) of the polymer-bound benzoic acid 15 and 5 mL of dichloromethane. After stirring under a flow of argon for 7 days, at RT, the solid was filtered and washed with methanol/acetone, dicholoromethane, and methanol to yield 150 mg of the benzamide bound polymer 17.

Iodinolysis: 0.35 mmol of N-(2-(diethylamino)ethyl)benzamide and 0.08 mmol of 4-iodobenzoic acid per gram of polymer Poly-(4-{dibutyl[2-(3- and 4-vinylphenyl)ethyl] stannyl}N-succinimidyl ester)-co-divinylbenzene (18)

Into a 50-mL round-bottom flask were placed 60 mg (0.3 mmol) of 1-(3-dimethylamino)propyl-3-ethylcarbodiimide hydrochloride (EDC), 35 mg (0.3 mmol) of N-hydroxysuccinimide (NHS), 52 mg (0.4 mmol) of collidine, and 7 mL of dichloromethane. This was stirred for 10 min. for complete dissolution. Then 50 mg (0.03 mmol) of the p-benzoic acid polymer 15 was added followed by stirring at RT for 70 h. The polymer was filtered and washed with methanol and acetone several times, to yield 46 mg of the activated ester polymer 18.

IR (DRIFT, solid): 1773 cm$^{-1}$, 1743 cm$^{-1}$ C=O

Poly-(4-{dibutyl[2-(3- and 4-vinylphenyl)ethyl] stannyl}N,N-diethylethylenediamino benzamidyl)-co-divinylbenzene (17)

Into a 25 mL vial were placed 32 mg of the polymer-bound activated ester 18, 31 mg (0.2 mmol) of diisopropylethylamine (DIPEA) and 37 mg (0.3 mmol) of N,N-diethylethylenediamine. After addition of 2 mL of dichloromethane, the reaction was allowed to stir for 23 h at RT. The solid was filtered and washed with methanol, water, methanol/water/acetone, and methanol to yield 27 mg of the benzamide bound polymer 17. Iodinolysis: 0.43 mmol of the N-(2-(diethylamino)ethyl)benzamide and 0.09 mmol of the 4-iodobenzoic acid per gram of polymer.

Poly-(4S,5S)-2-(5-{dibutyl[2-(4-vinylphenyl)ethyl] stannyl}-2,3-dihydrobenzofuran-7-yl)-3,4-dimethyl-5-phenyl-1,3-oxazolidine-co-divinylbenzene (19)

The previously prepared 20 (700 mg, 1.88 mmol), was added into a three-necked 200 mL round-bottom flask, equipped with a T-bore stopcock, a rubber septum and a powder addition side arm containing 850 mg of chlorostannane polymer (1.47 mmol SnCl/g of polymer). Under a flow of argon, 45 mL of freshly distilled dry THF was added by syringe. The flask and its contents were outgased three times at dry ice/acetone temperatures and an argon atmosphere was introduced. To the solution of 3 in THF at −78° C., n-butyl-lithium (0.75 mL, 1.88 mmol, 2.5 M) was added dropwise with the resultant formation of a yellow color. After 2 h at −78° C., the polymer was tipped into the THF solution, and the suspension was allowed to stir for 18 h and warm slowly to RT. To the suspension, about 5 mL of methanol was added and the suspension was filtered. The solid was washed with methanol, water, methanol/water/acetone, methanol/acetone and methanol several times to yield 1.6 g of 19. $^{119}$Sn MAS NMR (ppm): −39.3, IR (DRIFT, cm$^{-1}$): 1014, 1061

Poly-5-{dibutyl[2-(4-vinylphenyl)ethyl]stannyl}-2,3-dihydrobenzofuran-7-carbaldehyde-co-divinylbenzene (21)

To a sample of 19 (0.975 g) in a 5 dram sample vial, acetic acid (5 mL), methanol (5 mL), and water (1.3 mL) were added and the reaction was stirred for four hours and filtered. The insoluble material was washed with methanol, water, and acetone and dried under vacuum for 2 hours to yield 558 mg of a light yellow solid.
$^{119}$Sn MAS NMR (ppm): −39.2 IR (DRIFTS (cm$^{-1}$): 1686, 1648

Benzamide Library

The following library of benzamides was produced using a procedure similar to that for the preparation of 17:

| Amine | Iodinolysis mmol/g of polymer | | $^{119}$Sn NMR (ppm) | IR (cm$^{-1}$) C=O stretch |
|---|---|---|---|---|
| | 4-iodobenz-amide | 4-iodobenzoic Acid | | |
| N,N-Dimethylethyl-enediamine | — | — | −41.2 | 1658 |
| N,N-Diethylethyl-enediamine | 0.40 | 0.10 | −41.2 | 1653 |
| N,N-Diisopropylethyl-enediamine | 0.35 | 0.20 | −41.4 | — |
| N,N-Di-n-butylethyl-enediamine | — | — | −41.2 | — |
| 1-(2-amino-ethyl)pyrrolidine | 0.32 | 0.29 | −41.2 | 1658 |
| 1-(2-amino-ethyl)piperidine | 0.41 | 0.17 | −41.2 | 1653 |
| 4-(2-amino-ethyl)morpholine | 0.54 | 0.11 | −41.1 | 1643 |

EXAMPLE 3

Purification of Benzamides from Iodinolysis

To approximately 4 mg of poly-(4-{dibutyl[2-(3- and 4-vinylphenyl)ethyl]stannyl}4-(2-aminoethyl)morphobenzamidyl)-co-divinylbenzene in a 25 mL vial was added ~2 mL of CH$_3$CN and ~1 mL of 0.1M I$_2$/CH$_3$CN. After shaking this suspension for 2 h, sufficient 0.2 M sodium thiosulfate was added to discharge the iodine colour. The resultant reaction mixture was then diluted four fold using equal volumes of methanol and 1M NaOH. About 2 mL of this solution was passed through a reverse phase C-18 SepPak (Adsorbex RP-18 (100 mg)). An HPLC analysis of this solution showed one peak consistent with 4-iodobenzaldehyde. The C-18 SepPak column was then washed with about 2 mL of water. HPLC trace of this solution showed one peak, 4-iodobenzoic acid. A wash with about 2 mL of ethanol produced a solution which upon HPLC analysis showed one peak, 4-iodo-N-(2-morpholin-4-ylethyl)benzamide.

EXAMPLE 4

Preparation of (E)-iodo-3-triisopropylsiloxy-1-propene

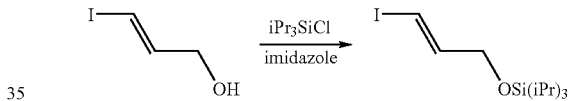

A two-necked, round bottom flask was charged with (E)-3-iodo-2-propene-1-ol (1 g, 5.44 mmol) under a flow of N$_2$. Dry CH$_2$Cl$_2$ (10 mL) was added followed by imidazole (0.369 g, 5.44 mmol) and chlorotriisopropylsilane (1.17 mL, 5.44 mmol). The contents of the flask were stirred at room temperature for 3 h under an atmosphere of nitrogen. The reaction mixture was then added into a separatory funnel and washed several times with water. The organic layer was dried with MgSO$_4$, filtered and dried in vacuo. The resulting oil was flash distilled at 88-92° C. @ 0.35 mmHg to give 1.08 g (58% yield) of the pure oil.

$^1$H NMR (400 MHz, CDCl$_3$, δ): 1.04 (21H, —CH(CH$_3$)$_2$ and —CH(CH$_3$)$_2$, 4.18 (2H, dd, ICH=CH—CH$_2$—, $^3J_{H-H}$=4.2 Hz, $^4J_{H-H}$=1.8 Hz), 6.31 (1H, dt, ICH=CH—CH$_2$—, $^3J_{H-H}$=14 Hz, $^4J_{H-H}$=1.8 Hz), 6.59 (1H, dt, ICH=CH—CH$_2$—, $^3J_{H-H}$=14 Hz, $^4J_{H-H}$=4.2 Hz). $^{13}$C NMR (400 MHz, CDCl$_3$, δ): 12.2 (—CH(CH$_3$)$_2$), 18.2 (—CH(CH$_3$)$_2$), 65.8 (ICH=CH—CH$_2$—), 75.8 (ICH=CH—CH$_2$—), 145.2 (ICH=CH—CH$_2$—).

Preparation of Polymer A

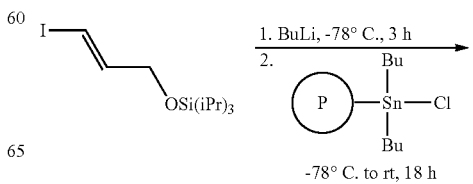

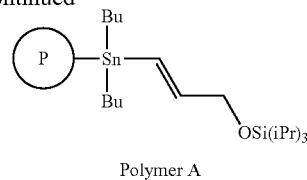

Polymer A

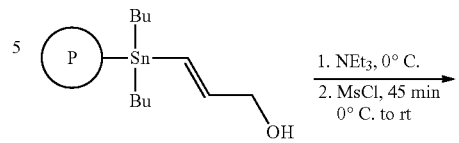

Polymer B
0.56 mmol/g

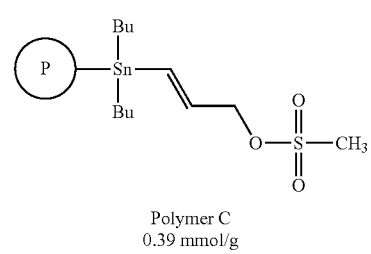

Polymer C
0.39 mmol/g (E)-1-iodo-3-triisopropylsiloxy-1-propene (2.21 g, 6.49 mmol), was added into a three-necked, 200 mL round-bottom flask, equipped with a $N_2$ inlet, a rubber septum and a powder addition side arm containing 3 g of chlorostannane polymer (1.73 mmol/g, 5.19 mmol of SnCl). The flask was evacuated and placed under nitrogen. Under an atmosphere of $N_2$, 80 mL of freshly distilled, dry THF was added via syringe. The flask and its contents were outgased three times at dry ice/acetone temperatures to ensure an atmosphere of $N_2$. To this solution a −78° C., n-butyllithium (2.69 mL, 2.01 M, 5.41 mmol) was added dropwise. After 3 h at −78° C., the polymer was tipped into the THF solution. This suspension was allowed to stir for 18 h and warm slowly to rt. To the suspension approximately 3 mL of methanol was added and the suspension was filtered. The solid was washed with methanol, methanol/water, water, water/acetone and acetone several times to yield 3.15 g of Polymer A.

MAS $^{119}$Sn NMR spectrum (PhCH$_3$): −47.5 ppm.

IR spectrum (DRIFT, solid, cm$^{-1}$): 1070, 1097 (C—O); 997 (trans CH═CH)

Conversion of Polymer A to Polymer B

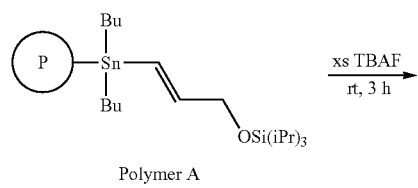

Polymer A

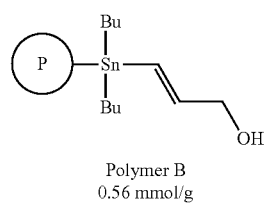

Polymer B
0.56 mmol/g

Polymer A (1 g), was added into a two-necked, 100 mL round-bottom flask, equipped with a $N_2$ inlet and a rubber septum. The flask was evacuated and placed under nitrogen. Under an atmosphere of $N_2$, 20 mL of freshly distilled, dry THF was added via syringe. An excess of tetra-butyl ammonium fluoride (2 mL) was the added via syringe resulting in a yellow solution. The suspension was allowed to stir at room temperature for 3 h at which point the suspension was filtered and the solid was washed with methanol, methanol/water, water, water/acetone and acetone several times to yield 0.983 g of Polymer B. MAS $^{119}$Sn NMR spectrum (PhCH$_3$): −47.5 ppm. IR spectrum. (DRIFT, solid, cm$^{-1}$): 3297 (OH), 1074 (C—O), 992 (trans CH═CH) Iodinolysis: 0.558 mmol/g of (E)-3-iodo-2-propene-1-ol per gram of polymer.

Conversion of Polymer B to Polymer C

A 50 mL round bottom flask was charged with Polymer B (0.60 g), 10 mL of THF and 1.39 mL of NEt$_3$ (0.996 mmol). The suspension was cooled to 0° C. in an ice bath and mesyl chloride (0.848 mL, 10.96 mmol) was added dropwise. The solution turned bright yellow within 5 minutes. The ice bath was removed and the solution allowed to warm to room temperature. After 45 minutes, the suspension was filtered and the solid was washed with methanol, methanol/water, water, water/acetone and acetone several times to yield 0.622 g of Polymer C which was stored in the freezer. MAS $^{119}$Sn NMR spectrum (PhCH$_3$): −48.1 ppm (major), 142.6 ppm (minor). IR spectrum (DRIFT, solid, cm$^{-1}$): 1359, 1175 (S═O), 997 (trans CH═CH)

Iodinolysis: 0.392 mmol/g of (E)-3-iodo-2-propene-1-yl methanesulfonate per gram of polymer.

Preparation of Polymer D

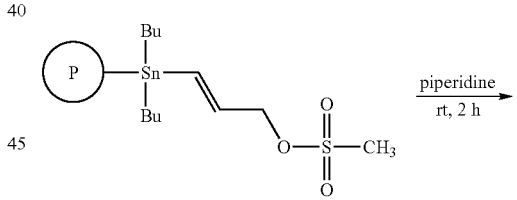

Polymer C
0.39 mmol/g

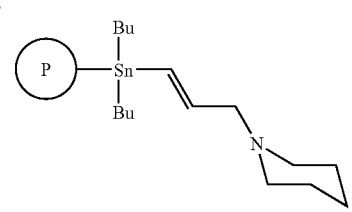

Polymer D
0.20 mmol/g

A 50 mL round bottom flask was charged with Polymer C (0.30 g), 10 mL of THF and an excess of piperidine (0.38 g, 4.41 mmol). The suspension was allowed to stir for 2 h at room temperature after which the suspension was filtered and the solid was washed with methanol, methanol/water, water, water/acetone and acetone several times to yield 0.309 g of Polymer D.

MAS $^{119}$Sn NMR spectrum (PhCH$_3$): −49.9 ppm. IR spectrum (DRIFT, solid, cm$^{-1}$): 965 (trans CH=CH) Iodinolysis: 0.208 mmol/g of N-(E)-3-iodo-2-propene-1-yl piperidine per gram of polymer.

Typical Procedure for the Iodinolysis of Polymers B, C and D

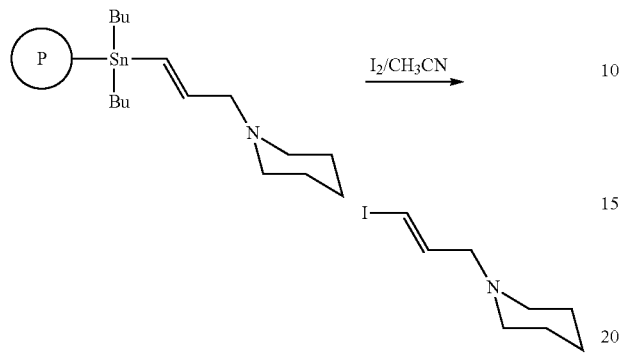

Approximately 1 mL of I$_2$/CH$_3$CN (0.1 M) was added to a suspension of the selected polymer (25 mg) in ~2 mL CH$_3$CN. After shaking for 2 h at rt, an aqueous solution of sodium thiosulfate (0.2 M) was added until a colorless solution was obtained. The resulting solution was diluted to 25 mL with CH$_3$CN. A portion of this suspension was filtered through a Whatman 0.45 μm nylon syringe filter. This solution was analyzed by HPLC and compared to a 1 mM standard solution of an authentic sample of the corresponding iodo compound.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula 1:

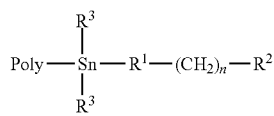

wherein

Poly represents a polymer selected from the group polyethylene glycol, polystyrene, polyamide, polypeptide, polyurethane, poly(ethylene-co-vinyl acetate), polyethylene, polystyrene/rubber and poly(ethylene-co-propylene);

R$^1$ represents alkenyl;

R$^2$ represents —NR$^4$R$^5$, phosphate, phosphite, phosphine, XR$^{5'}$, Z, or R$^2$ is represented by formula 2:

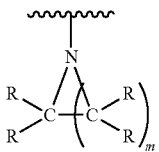

wherein m is 1-8; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsllifonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, —COR$^6$, —C(O)$_2$R$^6$, —C(O)N(R$^6$)$_2$, —N(R$^6$)C(O)R$^6$, —OC(O)N(R$^6$)$_2$, —N(R$^6$)C(O)$_2$R$^7$, —C(S)N(R$^6$)$_2$, —N(R$^6$)C(S)R$^6$, —OC(S)N(R$^6$)$_2$, —N(R$^6$)C(S)OR$^7$, —N(R$^6$)C(O)N(R$^6$)$_2$, —N(R$^6$)C(S)N(R$^6$)$_2$, or —(CH$_2$)$_q$—R$_{80}$; wherein q is 1-10; R$_{80}$ represents an optionally substituted aryl, cycloalkyl, cycloalkenyl, heterocyclyl, or polycyclyl; R$^6$ represents independently for each occurence H, alkyl, alkenyl, aryl, or aralkyl; and R$^7$ represents independently for each occurrence alkyl, alkenyl, aryl, or aralkyl;

X is S, Se, or AsR$^5$;

Z is a malonate, β-ketoester, α-nitroester, α-cyanoester, α-phosphonoester, or α-ketophosphonate;

n is 1-15;

R$^3$ represents independently for each occurrence alkyl, aralkyl, alkenyl or alkynyl;

R$^4$ and R$^5$ represent independently for each occurrence hydrogen, alkyl, heteroalkyl, cycloalkyl, heterocyloalkyl, alkenyl, alkynyl, aryl, heteroaryl, aralkyl, or heteroaralkyl; and R$^{5'}$ represents alkyl, heteroalkyl, cycloalkyl, heterocyloalkyl, alkenyl, alkynyl, aryl, heteroaryl, aralkyl, or heteroaralkyl.

2. The compound of claim 1, wherein n is 1-5.

3. The compound of claim 1, wherein n is 1.

4. The compound of claim 1, wherein R$^1$ is —CH=CH—.

5. The compound of claim 1, wherein R$^3$ is alkyl.

6. The compound of claim 1, wherein R$^3$ is n-butyl.

7. The compound of claim 1, wherein R$^1$ is —HC=CH—, R$^3$ is alkyl, n is 1, poly is polystyrene, and R$^2$ is —NR$^4$R$^5$.

8. The compound of claim 1, wherein R$^2$ is —NR$^4$R$^5$ or XR$^{5'}$.

9. The compound of claim 1, wherein R$^2$ is —NR$^4$R$^5$.

10. The compound of claim 1, wherein R$^2$ is an amino group of a nucleotide, nucleoside, nucleic acid, carbohydrate, purine, pyrimidine or amino acid.

11. The compound of claim 1, wherein R$^1$ is —HC=CH—, R$^3$ is alkyl, n is 1, said polymer is polystyrene, and R$^2$ is optionally substituted 1-piperidinyl.

12. The compound of claim 1, wherein R$^2$ is XR$^{5'}$, wherein X is S.

13. The compound of claim 1, wherein the polymer of structure 1 is functionalized by the moiety —Sn(R$^3$)$_2$R$^1$(CH$_2$)nR$^2$ on a plurality of monomeric units of the polymer.

14. The compound of claim 1, wherein R$^2$ is an amino group of a peptide.

15. The compound of claim 1, wherein R$^2$ is an amino group of an antibody.

16. The compound of claim 1, wherein poly is polystyrene.

17. The compound of claim 1, wherein $R^2$ is represented by formula 2:

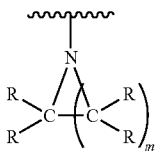

2 wherein m is 3 or 4; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, —$COR^6$, —$CO_2R^6$, —$C(O)N(R^6)_2$, —$N(R^6)C(O)R^6$, —$OC(O)N(R^6)_2$, —$N(R^6)CO_2R^7$, —$C(S)N(R^6)_2$, —$N(R^6)C(S)R^6$, —$OC(S)N(R^6)_2$, —$N(R^6)C(S)OR^7$, —$N(R^6)C(O)N(R^6)_2$, —$N(R^6)C(S)N(R^6)_2$, or —$(CH_2)_q$—$R_{80}$; wherein q is 1-10; $R_{80}$ represents an optionally substituted aryl, cycloalkyl, cycloalkenyl, heterocyclyl, or polycyclyl; $R^6$ represents independently for each occurence H, alkyl, alkenyl, aryl, or aralkyl; $R^7$ represents independently for each occurrence alkyl, alkenyl, aryl, or aralkyl; and poly is polystyrene.

18. A method of synthesizing a polymer-bound prosthetic, group, wherein the polymer-bound prosthetic group is the compound of claim 1, comprising the steps of:
combining a first compound and a polymer to give a first polymer-bound compound; and combining a second compound with said first polymer-bound compound to give a second polymer-bound compound comprising a functionalized prosthetic group, wherein said second compound is an amine, phosphate, phosphite, phosphine, alcohol, phenol, thiol, alkylselenide, arylselenide, bis(alkyl)arsenide, bis(aryl)arsenide, malonate, β-ketoester, α-nitroester, α-cyanoester, α-phosphonoester, or α-ketophosphonate, or an anion derived from any of them; said polymer comprises a tin chloride moiety; and said first compound is represented by formula 3:

$$M-R^1—(CH_2)_n—R^2 \quad 3$$

wherein
M is a cation;
$R^1$ represents alkenyl;
$R^2$ is $OSi(alkyl)_3$, OMEM, acyloxy, or OBn; and
n is 1-15.

19. The method of claim 18, wherein n is 1-5.
20. The method of claim 18, wherein n is 1.
21. The method of claim 18, wherein M is an alkali metal cation or alkaline earth metal cation.
22. The method of claim 18, wherein M is Li, Na, K, ZnCl, ZnBr, MgBr, or MgCl.
23. The method of claim 18, wherein $R^2$ is $OSi(alkyl)_3$.
24. The method of claim 18, wherein $R^2$ is $OSi(iPr)_3$.
25. The method of claim 18, wherein $R^1$ is —CH=CH—.
26. The method of claim 18, wherein said second compound is an amine, alcohol, phenol, thiol, malonate, β-ketoester, or an anion derived from any of them.

27. The method of claim 18, wherein said second compound is an amine, alcohol, or an anion derived from any of them.
28. The method of claim 18, wherein said second compound is an amine or an anion derived therefrom.
29. The method of claim 18, wherein said functionalized prosthetic group is represented by formula 2:

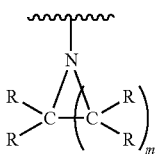

2 wherein m is 1-8; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, —$COR^6$, —$CO_2R^6$, —$C(O)N(R^6)_2$, —$N(R^6)C(O)R^6$, $OC(O)N(R^6)_2$, —$N(R^6)CO_2R^7$, —$C(S)N(R^6)_2$, —$N(R^6)C(S)R^6$, —$OC(S)N(R^6)_2$, —$N(R^6)C(S)OR^7$, —$N(R^6)C(O)N(R^6)_2$, —$N(R^6)C(S)N(R^6)_2$, or —$(CH_2)_q$—$R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; and $R^7$ represents independently for each occurrence alkyl, alkenyl, aryl, or aralkyl.

30. The method of claim 18, wherein said functionalized prosthetic group is represented by formula 2:

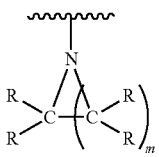

2 wherein m is 3 or 4; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, —$COR^6$, —$CO_2R^6$, —$C(O)N(R^6)_2$, —$N(R^6)C(O)R^6$, $OC(O)N(R^6)_2$, —$N(R^6)CO_2R^7$, —$C(S)N(R^6)_2$, —$N(R^6)C(S)R^6$, —$OC(S)N(R^6)_2$, —$N(R^6)C(S)OR^7$, —$N(R^6)C(O)N(R^6)_2$, —$N(R^6)C(S)N(R^6)_2$, or —$(CH_2)_q$—$R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; and $R^7$ represents independently for each occurrence alkyl, alkenyl, aryl, or aralkyl.

31. The method of claim 18, wherein said functionalized prosthetic group is optionally substituted 1-piperidinyl.

32. The method of claim 18, wherein said polymer comprises a tin chloride moiety and polyethylene glycol, polystyrene, polyamide, or polypeptide.

33. The method of claim 18, wherein said polymer comprises a tin chloride moiety and polystyrene, polyurethane, poly(ethylene-co-vinyl acetate), polyethylene, polystyrene/rubber, or poly(ethylene-co-propylene).

34. The method of claim 18, wherein said polymer comprises a tin chloride moiety and polystyrene.

35. The method of claim 18, wherein said polymer comprises a dibutyltin chloride moiety and polystyrene.

36. A method for preparing a radiopharmaceutical compound from a polymer-bound compound comprising a functionalized prosthetic group, comprising the steps of:
mixing a radioisotope, an oxidant, and a polymer-bound compound comprising a functionalized prosthetic group, wherein said polymer-bound compound comprising a functionalized prosthetic group is represented by formula 1:

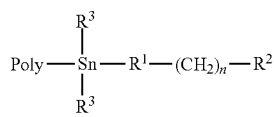

1 wherein
Poly represents a polymer selected from the group polyethylene glycol, polystyrene, polyamide, polypeptide, polyurethane, poly(ethylene-co-vinyl acetate), polyethylene, polystyrene/rubber and poly(ethylene-co-propylene);
$R^1$ represents alkenyl:
$R^2$ represents $-NR^4R^5$, phosphate, phosphate, phosphine, $XR^{5'}$, Z, or $R^2$ is represented by formula 2:

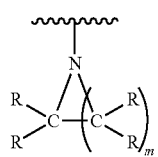

2 wherein m is 1-8; R represents independently for each occurrence hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carboxamide, anhydride, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, hydroxamic acid, imide, oxime, sulfonamide, $-COR^6$, $-CO_2R^6$, $-C(O)N(R^6)_2$, $-N(R^6)C(O)R^6$, $-OC(O)N(R^6)_2$, $-N(R^6)CO_2R^7$, $-C(S)N(R^6)_2$, $-N(R^6)C(S)R^6$, $-OC(S)N(R^6)_2$, $-N(R^6)C(S)OR^7$, $-N(R^6)C(O)N(R^6)_2$, $-N(R^6)C(S)N(R^6)_2$, or $-(CH_2)_q-R_{80}$; wherein q is 1-10; $R_{80}$ represents an optionally substituted aryl, cycloalkyl, cycloalkenyl, heterocyclyl, or polycyclyl; $R^6$ represents independently for each occurrence H, alkyl, alkenyl, aryl, or aralkyl; and $R^7$ represents independently for each occurrence alkyl, alkenyl, aryl, or aralkyl;

X is S, Se, or $AsR^5$;

Z is a malonate, β-ketoester, α-nitroester, α-cyanoester, α-phosphonoester, or α-ketophosphonate;

n is 1-15;

$R^3$ represents independently for each occurrence alkyl, aralkyl, alkenyl or alkynyl;

$R^4$ and $R^5$ represent independently for each occurrence hydrogen, alkyl, heteroalkyl, cycloalkyl, heterocycloalkyl, alkenyl, alkynyl, aryl, heteroaryl, aralkyl, or heteroaralkyl; and $R^{5'}$ represents alkyl, heteroalkyl, cycloalkyl, heterocycloalkyl, alkenyl, alkynyl, aryl, heteroaryl, aralkyl, or heteroaralkyl.

37. The method of claim 36, wherein said oxidant is chloramine-T in ethanol/water with or without acetic acid, N-chlorosuccinimide with acetic acid in methanol, tert-butylhydroperoxide with acetic acid in chloroform, Iodogen with a phosphate buffer, or iodobeads with or without acetic acid in methanol.

38. The method of claim 36, wherein said radioisotope is $^{18}F$, $^{11}C$, $^{76}Br$, $^{211}At$, $^{123}I$, $^{131}I$ or $^{125}I$.

39. The method of claim 36, wherein said radioisotope is $^{211}At$, $^{131}I$, $^{123}I$, or $^{18}F$.

40. The method of claim 36, wherein said radioisotope is $^{211}At$.

41. The method of claim 36, wherein said radioisotope, is $^{131}I$.

42. The method of claim 36, wherein said radiopharmaceutical compound formed by this process is produced at the no-carrier-added level and has a specific activity equal to about the specific activity level of the source of said radioisotope.

43. The method of claim 36, wherein said radiopharmaceutical compound is isotopically pure.

44. The method of claim 36, wherein said radiopharmaceutical compound is a radiolabeled peptide or protein; and said radiopharmaceutical compound isotopically pure.

45. The method of claim 36, wherein said radiopharmaceutical compound is a radiolabeled antibody; and said radiopharmaceutical compound is isotopically pure.

46. The method of claim 36, wherein said radiopharmaceutical compound is a radiolabeled nucleotide or nucleoside; and said radiopharmaceutical compound is isotopically pure.

* * * * *